US007244601B2

(12) United States Patent
Gilbert et al.

(10) Patent No.: US 7,244,601 B2
(45) Date of Patent: Jul. 17, 2007

(54) FUSION PROTEINS FOR USE IN ENZYMATIC SYNTHESIS OF OLIGOSACCHARIDES

(75) Inventors: Michel Gilbert, Hull (CA); N. Martin Young, Gloucester (CA); Warren W. Wakarchuk, Gloucester (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/211,691

(22) Filed: Dec. 14, 1998

(65) Prior Publication Data

US 2002/0034805 A1 Mar. 21, 2002

Related U.S. Application Data

(60) Provisional application No. 60/069,443, filed on Dec. 15, 1997.

(51) Int. Cl.
| | |
|---|---|
| C12N 9/10 | (2006.01) |
| C12N 1/12 | (2006.01) |
| C12N 15/00 | (2006.01) |
| C07H 21/04 | (2006.01) |

(52) U.S. Cl. .............................. 435/193; 435/4; 435/6; 435/69.1; 435/183; 435/194; 435/252.3; 435/320.1; 530/350; 536/23.2; 536/23.4

(58) Field of Classification Search ................ 435/193, 435/183, 200, 325, 320.1, 4, 6, 69.1, 194, 435/196, 252.3; 536/23.2; 530/350; 430/4, 430/6, 69.1, 183, 193, 194, 196, 252.3, 320.1
See application file for complete search history.

(56) References Cited

U.S. PATENT DOCUMENTS

| 5,032,519 A | 7/1991 | Paulson et al. ............. 435/193 |
| 5,352,670 A | 10/1994 | Venot et al. .................. 514/54 |
| 5,374,541 A | 12/1994 | Wong et al. .................. 435/74 |
| 5,516,665 A | 5/1996 | Wong .......................... 435/97 |

FOREIGN PATENT DOCUMENTS

| WO | WO 96 21038 | 7/1996 |
| WO | WO 96 32491 | 10/1996 |
| WO | WO 96 35801 A | 11/1996 |
| WO | WO 96 40971 A | 12/1996 |
| WO | WO 98 07837 A | 2/1998 |

OTHER PUBLICATIONS

Ito et al., "Synthesis of bioactive sialosides," *Pure & Appl. Chem.* 65(4):753-762 (1993)..
Aoki et al., Analysis of the substrate binding sites of human galactosyltransferase by protein engineering, *EMBO. J.* 9: 3171-3178 (1990).
Harduin-Lepers et al., "Mini Review 1994, the year of the sialyltransferases," *Glycobiology* 5(8): 741-758, (1995).
Natsuka and Lowe, "Enzymes involved in mammalian oligosaccharide biosynthesis," *Curr. Opin. Struct. Biol.* 4: 683-691, (1994).
Zu et al., "Use of Site-Directed Mutagenesis to Identify the Galactosyltransferase Binding Sites for UDP-Galactose," *Biochem. Biophys. Res. Comm.* 206(1): 362-369 (1995).
Seto et al., "Expression of a recombinant human glycosyltransferase from a synthetic gene and its utilization for synthesis of the human blood group B trisaccharide," *Eur. J. Biochem.* 234: 323-328 (1995).
Seto et al., "Sequential Interchange of Four Amino Acids from Blood Group B to Blood Group A Glycosyltransferase Boosts Catalytic Activity and Progressively Modifies Substrate Recognition in Human Recombinant Enzymes," *Eur. J. Biochem* 272: 14133-141388 (1997).
Gilbert et al., "Purification and characterization of the recombinant CMP-sialic acid synthetase from *Neisseria meningitidis*," *Biotechnol. Lett.* 19: 417-420 (1997).
Gilbert et al., "Cloning of the Lipooligosaccharide a-2-3-Sialyltransferase from the Bacterial Pathogens *Neisseria meningitidis* and *Neisseria gonorrhoeae*," *J. Biol. Chem.* 271: 28271-28276 (1996).
Gilbert et al., "Characterization of a recombinant *Neisseria meningitidis* a-2,3-sialyltransferase and its acceptor specificity," *Eur. J. Biochem.* 249: 187-194 (1997).
Gilbert et al., "The synthesis of sialylated oligosaccharides using a CMP-Neu5Ac synthetase/sialyltransferase fusion,"*Nature Biotechnol..* 16: 769-772 (1998).
Wakarchuk et al., "Functional Relationships of the Genetic Locus Encoding the Glycosyltransferase Enzymes Involved in Expression of the Lacto-N-neotetraose Terminal Lipopolysaccharide Structure in *Neisseria meningitidis*," *J. of Biol. Chem.* vol. 271, No. 32: 19166-19173 (1996).
Stevenson et al., "Organization of the *Escherichia coli* K-12 Gene Cluster Responsible for Production of the Extracellular Polysaccharide Colanic Acid," *J. Bacteriol.* 178: 4885-4893, (1996).
Bülow, L. and Mosbach, K. "Multienzyme systems obtained by gene fusion," *TIBTECH* Jul. 1991, pp. 226-231, vol. 9.
Guo, Z. and Wang, P.G. "Utilization of glycosyltransferases to change oligosaccharide structures," *Appl. Biochem. & Biotechnol.* 1997, pp. 1-20, vol. 68.
Fang et al., "A unique chemoenzymatic synthesis of α-galactosyl epitope derivatives containing free amino groups: Efficient separation and further manipulation," J. Org. Chem. 1999, pp. 4089-4094, vol. 64.
Chen et al., "Changing the donor cofactor of bovine α1,3-galactosyltransferase by fusion with UDP-galactose 4-epimerase," J. Biol. Chem. 2000, pp. 31594-31600, vol. 275.
Warner, Thomas G., "Sweet success with tethered enzyme catalysis," Nature Biotechnology, Aug. 1998, pp. 720-721, vol. 16.

*Primary Examiner*—Manjunath N Rao
(74) *Attorney, Agent, or Firm*—Townsend and Townsend and Crew, LLP

(57) ABSTRACT

This invention provides fusion polypeptides that include a glycosyltransferase catalytic domain and a catalytic domain from an accessory enzyme that is involved in making a substrate for a glycosyltransferase reaction. Nucleic acids that encode the fusion polypeptides are also provided, as are host cells for expressing the fusion polypeptides of the invention.

12 Claims, 4 Drawing Sheets

Figure 2

```
      ATGCAAAACCACGTTATCAGCTTAGCTTCCGCCGCAGAACGCAGGGCGCACATTGCCGAT
  1   ---------+---------+---------+---------+---------+---------+  60
      TACGTTTTGGTGCAATAGTCGAATCGAAGGCGGCGTCTTGCGTCCCGCGTGTAACGGCTA
       M  Q  N  H  V  I  S  L  A  S  A  A  E  R  R  A  H  I  A  D   -

ACCTTCGGCAGGCACGGCATCCCGTTTCAGTTTTTCGACGCACTGATGCCGTCTGAAAGG
 61   ---------+---------+---------+---------+---------+---------+ 120
      TGGAAGCCGTCCGTGCCGTAGGGCAAAGTCAAAAAGCTGCGTGACTACGGCAGACTTTCC
       T  F  G  R  H  G  I  P  F  Q  F  F  D  A  L  M  P  S  E  R   -

CTGGAACAGGCAATGGCGGAACTCGTCCCCGGCTTGTCGGCGCACCCCTATTTGAGCGGA
121   ---------+---------+---------+---------+---------+---------+ 180
      GACCTTGTCCGTTACCGCCTTGAGCAGGGGCCGAACAGCCGCGTGGGGATAAACTCGCCT
       L  E  Q  A  M  A  E  L  V  P  G  L  S  A  H  P  Y  L  S  G   -

GTGGAAAAAGCCTGCTTTATGAGCCACGCCGTATTGTGGAAGCAGGCATTGGACGAAGGT
181   ---------+---------+---------+---------+---------+---------+ 240
      CACCTTTTTCGGACGAAATACTCGGTGCGGCATAACACCTTCGTCCGTAACCTGCTTCCA
       V  E  K  A  C  F  M  S  H  A  V  L  W  K  Q  A  L  D  E  G   -

CTGCCGTATATCACCGTATTTGAGGACGACGTTTTACTCGGCGAAGGTGAGGAAAAATTC
241   ---------+---------+---------+---------+---------+---------+ 300
      GACGGCATATAGTGGCATAAACTCCTGCTGCAAAATGAGCCGCTTCCACTCCTTTTTAAG
       L  P  Y  I  T  V  F  E  D  D  V  L  L  G  E  G  E  E  K  F   -

CTTGCCGAAGACGCTTGGCTGCAAGAACGCTTTGACCCGGATACCGCCTTTATCGTCCGC
301   ---------+---------+---------+---------+---------+---------+ 360
      GAACGGCTTCTGCGAACCGACGTTCTTGCGAAACTGGGCCTATGGCGGAAATAGCAGGCG
       L  A  E  D  A  W  L  Q  E  R  F  D  P  D  T  A  F  I  V  R   -

TTGGAAACGATGTTTATGCACGTCCTGACCTCGCCCTCCGGCGTGGCGGATTACTGCGGG
361   ---------+---------+---------+---------+---------+---------+ 420
      AACCTTTGCTACAAATACGTGCAGGACTGGAGCGGGAGGCCGCACCGCCTAATGACGCCC
       L  E  T  M  F  M  H  V  L  T  S  P  S  G  V  A  D  Y  C  G   -

CGCGCCTTTCCGCTGTTGGAAAGCGAACACTGGGGGACGGCGGGCTATATCATTTCCCGA
421   ---------+---------+---------+---------+---------+---------+ 480
      GCGCGGAAAGGCGACAACCTTTCGCTTGTGACCCCCTGCCGCCCGATATAGTAAAGGGCT
       R  A  F  P  L  L  E  S  E  H  W  G  T  A  G  Y  I  I  S  R   -

AAAGCGATGCGGTTTTTCCTGGACAGGTTTGCCGCCCTGCCGCCCGAAGGGCTGCACCCC
481   ---------+---------+---------+---------+---------+---------+ 540
      TTTCGCTACGCCAAAAAGGACCTGTCCAAACGGCGGGACGGCGGGCTTCCCGACGTGGGG
       K  A  M  R  F  F  L  D  R  F  A  A  L  P  P  E  G  L  H  P   -

GTCGATCTGATGATGTTCAGCGATTTTTTCGACAGGGAAGGAATGCCGGTTTGCCAGCTC
541   ---------+---------+---------+---------+---------+-------;-+ 600
      CAGCTAGACTACTACAAGTCGCTAAAAAAGCTGTCCCTTCCTTACGGCCAAACGGTCGAG
       V  D  L  M  M  F  S  D  F  F  D  R  E  G  M  P  V  C  Q  L   -

AATCCCGCCTTGTGCGCCCAAGAGCTGCATTATGCCAAGTTTCACGACCAAAACAGCGCA
601   ---------+---------+---------+---------+---------+---------+ 660
      TTAGGGCGGAACACGCGGGTTCTCGACGTAATACGGTTCAAAGTGCTGGTTTTGTCGCGT
       N  P  A  L  C  A  Q  E  L  H  Y  A  K  F  H  D  Q  N  S  A   -

TTGGGCAGCCTGATCGAACACGACCGCCTCCTGAACCGCAAACAGCAAAGGCGCGATTCC
661   ---------+---------+---------+---------+---------+---------+ 720
      AACCCGTCGGACTAGCTTGTGCTGGCGGAGGACTTGGCGTTTGTCGTTTCCGCGCTAAGG
       L  G  S  L  I  E  H  D  R  L  L  N  R  K  Q  Q  R  R  D  S   -

CCCGCCAACACATTCAAACACCGCCTGATCCGCGCCTTGACCAAAATCAGCAGGGAAAGG
721   ---------+---------+---------+---------+---------+---------+ 780
      GGGCGGTTGTGTAAGTTTGTGGCGGACTAGGCGCGGAACTGGTTTTAGTCGTCCCTTTCC
       P  A  N  T  F  K  H  R  L  I  R  A  L  T  K  I  S  R  E  R   -

GAAAAACGCCGGCAAAGGCGCGAACAGTTCATTGTGCCTTTCCAATAA
781   ---------+---------+---------+---------+-------- 828
      CTTTTTGCGGCCGTTTCCGCGCTTGTCAAGTAACACGGAAAGGTTATT
       E  K  R  R  Q  R  R  E  Q  F  I  V  P  F  Q  *
```

Figure 4

A. 5' primer for amplification of *galE* for insertion into pCW at the BamHI site 5' GGGACAGGATCCATCGATGCTTAGGAGGTCATATGGCAATTTTAGTATTAGGTGGAGC 3'
       BamHI                                Met B. 3' primer for amplification of *galE* for fusion with *lgtB* insertion into pCW 5' GGGGGGGCTAGCGCCGCCTCCTCGATCATCGTACCCTTTTGG 3'
       NheI    Gly Gly C. 5' primer for amplification of *lgtB* for fusion with the 3' end of *galE*.

5' GGGGGGGCTAGCGTGCAAAACCACGTTATCAGCTTAGC
       NheI    Val

D. 3' primer for amplification of *lgtB* for fusion with *galE* and insertion into pCW 5' GGGGGGGTCGACCTATTATTGGAAAGGCACAATGAACTGTTCGCG
       SalI E. Junction region of the *galE-lgtB* fusion

```
         galE                    NheI                lgtB
5' CCA AAA GGG TAC GAT GAT CGA GGA GGC GGA GCT AGC GTG CAA AAC CAC GTT ATC AGC TTA GCT 3'
3' GGT TTT CCC ATG CTA CTA GCT CCT CCG CCT CGA TCG CAC GTT TTG GTG CAA TAG TCG AAT CGA 5'
    P   K   G   Y   D   D   R   G   G   G   A   S   V   Q   N   H   V   I   S   L   A
```

FUSION PROTEINS FOR USE IN ENZYMATIC SYNTHESIS OF OLIGOSACCHARIDES

CROSS REFERENCE TO RELATED APPLICATIONS

This application is a continuation-in-part of, and claims benefit of, U.S. Provisional Application No. 60/069,443, filed Dec. 15, 1997, which application is incorporated herein by reference for all purposes.

BACKGROUND OF THE INVENTION

1. Field of the Invention

This invention pertains to the field of enzymatic synthesis of oligosaccharides using fusion proteins that can catalyze more than one reaction involved in the enzymatic synthesis.

2. Background

Increased understanding of the role of carbohydrates as recognition elements on the surface of cells has led to increased interest in the production of carbohydrate molecules of defined structure. For instance, compounds comprising the sialyl Lewis ligands, sialyl Lewis$^x$ and sialyl Lewis$^a$ are present in leukocyte and non-leukocyte cell lines that bind to receptors such as the ELAM-1 and GMP 140 receptors. Polley et al., *Proc. Natl. Acad. Sci. USA* (1991) 88: 6224 and Phillips et al. (1990) *Science* 250: 1130, see, also, U.S. Pat. No. 5,753,631.

Because of interest in making desired carbohydrate structures, glycosyltransferases and their role in enzyme-catalyzed synthesis of carbohydrates are presently being extensively studied. These enzymes exhibit high specificity and are useful in forming carbohydrate structures of defined sequence. Consequently, glycosyltransferases are increasingly used as enzymatic catalysts in synthesis of a number of carbohydrates used for therapeutic and other purposes. In the application of enzymes to the field of synthetic carbohydrate chemistry, the use of glycosyltransferases for enzymatic synthesis of carbohydrate offers advantages over chemical methods due to the virtually complete stereoselectivity and linkage specificity offered by the enzymes (Ito et al. (1993) *Pure Appl. Chem.* 65: 753; and U.S. Pat. Nos. 5,352,670, and 5,374,541).

Chemoenzymatic syntheses of oligosaccharides and of corresponding derivatives therefore represent an interesting opportunity to develop novel therapeutic agents. However this approach is still hampered by the relatively poor availability of the required glycosyltransferases and the difficulty and cost of obtaining substrates for these enzymes. Large-scale enzymatic syntheses of oligosaccharides will also require large amounts of the accessory enzymes necessary for the synthesis of the sugar-nucleotides that are used as the donors by the glycosyltransferases. The present invention provides fusion proteins that simplify the purification of enzymes that are useful for enzymatic synthesis of oligosaccharides.

SUMMARY OF THE INVENTION

The present invention provides fusion polypeptides that are useful for enzymatic synthesis of oligosaccharides. The fusion polypeptides of the invention have a catalytic domain of a glycosyltransferase joined to a catalytic domain of an accessory enzyme. The accessory enzyme catalytic domain can, for example, catalyze a step in the formation of a nucleotide sugar which is a donor for the glycosyltransferase, or catalyze a reaction involved in a glycosyltransferase cycle.

In another embodiment, the invention provides nucleic acids that include a polynucleotide that encodes a fusion polypeptide. The fusion polypeptides have a catalytic domain of a glycosyltransferase, and a catalytic domain of an accessory enzyme. Expression cassettes and expression vectors that include the nucleic acids are also provided, as are host cells that contain the nucleic acids of the invention.

The invention also provides methods of producing a fusion polypeptide that has a catalytic domain of a glycosyltransferase and a catalytic domain of an accessory enzyme. The methods involve introducing a nucleic acid that encodes the fusion polypeptide into a host cell to produce a transformed host cell; and culturing the transformed host cell under conditions appropriate for expressing the fusion polypeptide.

BRIEF DESCRIPTION OF THE DRAWINGS

FIG. 2 shows the nucleotide (SEQ ID NO: 1) and deduced amino acid (SEQ ID NO: 2) sequences of lgtB from *Neisseria meningitidis*.

FIG. 4 shows primers (SEQ ID NO: 9–12) that were used in the construction of the UDP-Glc/Gal epimerase/β-1,4-Galactosyltransferase fusion protein. The nucleotide sequence (SEQ ID NO:16) and encoded amino acid sequence (SEQ ID NO:17) of the junction region of the galE-lgtB fusion are shown in FIG. 4E.

DETAILED DESCRIPTION

Definitions

Figure 1:
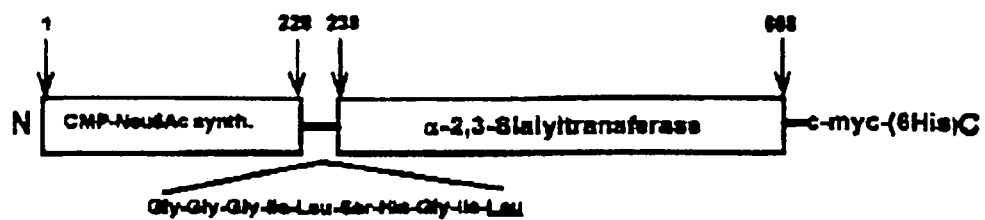
FIG. 1 is a diagram of recombinant sialyltransferase/CMP-NeuAc synthetase fusion protein of the invention. The C terminus of the CMP-Neu5Ac synthetase is linked covalently to the N terminus of the α-2,3-sialyltransferase through a 9-residue peptide linker. The first Met residue of the α-2,3-sialyltransferase was replaced by a Leu residue (underlined in the linker sequence (SEQ ID NO:13)). The C terminus of the fusion protein also includes a c-Myc epitope tag for immuno-detection and a His$_6$ (SEQ ID NO:14) tail for purification by IMAC. The total length of the fusion protein encoded by pFUS-01/2 is 625 residues.

The fusion proteins of the invention are useful for transferring a monosaccharide from a donor substrate to an acceptor molecule, and/or for forming a reactant that is involved in the saccharide transfer reaction. The addition generally takes place at the non-reducing end of an oligosaccharide or carbohydrate moiety on a biomolecule. Biomolecules as defined here include but are not limited to biologically significant molecules such as carbohydrates, proteins (e.g., glycoproteins), and lipids (e.g., glycolipids, phospholipids, sphingolipids and gangliosides).

The following abbreviations are used herein:

Ara=arabinosyl;

Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl (N-acetylneuraminyl).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond ($\alpha$ or $\beta$), the ring bond, the ring position of the reducing saccharide involved in the bond, and then the name or abbreviation of the reducing saccharide (e.g., GlcNAc). The linkage between two sugars may be expressed, for example, as 2,3, 2→3, or (2,3). Each saccharide is a pyranose or furanose.

Donor substrates for glycosyltransferases are activated nucleotide sugars. Such activated sugars generally consist of uridine, guanosine, and cytidine monophosphate or diphosphate derivatives of the sugars in which the nucleoside monophosphate or diphosphate serves as a leaving group. The donor substrate for sialyltransferases, for example, are activated sugar nucleotides comprising the desired sialic acid. For instance, in the case of NeuAc, the activated sugar is CMP-NeuAc.

The term "sialic acid" refers to 5-N-acetylneuraminic acid (NeuAc) or 5-N-glycolylneuraminic acid (NeuGc), as well as other sialic acids may be used in their place, however. For a review of different forms of sialic acid suitable in the present invention see, Schauer, *Methods in Enzymology*, 50: 64–89 (1987), and Schaur, *Advances in Carbohydrate Chemistry and Biochemistry*, 40: 131–234.

A "fusion glycosyltransferase polypeptide" of the invention is glycosyltransferase fusion polypeptide that contains a glycosyltransferase catalytic domain and a second catalytic domain from an accessory enzyme (e.g., a CMP-Neu5Ac synthetase or a UDP-Glucose 4' epimerase (galE)) and is capable of catalyzing the transfer of an oligosaccharide residue from a donor substrate (e.g., CMP-NeuAc or UDP-Gal) to an acceptor molecule. Typically, such polypeptides will be substantially similar to the exemplified proteins disclosed here.

An "accessory enzyme," as referred to herein, is an enzyme that is involved in catalyzing a reaction that, for example, forms a substrate for a glycosyltransferase. An accessory enzyme can, for example, catalyze the formation of a nucleotide sugar that is used as a donor moiety by a glycosyltransferase. An accessory enzyme can also be one that is used in the generation of a nucleotide triphosphate required for formation of a nucleotide sugar, or in the generation of the sugar which is incorporated into the nucleotide sugar.

A "catalytic domain" refers to a portion of an enzyme that is sufficient to catalyze an enzymatic reaction that is normally carried out by the enzyme. For example, a catalytic domain of a sialyltransferase will include a sufficient portion of the sialyltransferase to transfer a sialic acid residue from a donor to an acceptor saccharide. A catalytic domain can include an entire enzyme, a subsequence thereof, or can include additional amino acid sequences that are not attached to the enzyme or subsequence as found in nature.

Much of the nomenclature and general laboratory procedures required in this application can be found in Sambrook, et al., *Molecular Cloning: A Laboratory Manual* (2nd Ed.), Vol. 1–3, Cold Spring Harbor Laboratory, Cold Spring Harbor, N.Y., 1989. The manual is hereinafter referred to as "Sambrook et al."

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

A "heterologous sequence" or a "heterologous nucleic acid," as used herein, is one that originates from a source foreign to the particular host cell, or, if from the same source, is modified from its original form. Thus, a heterologous glycosyltransferase gene in a particular host cell includes a glycosyltransferase gene that is endogenous to the particular host cell but has been modified. Modification of the heterologous nucleic acid can occur, e.g., by treating the DNA with a restriction enzyme to generate a DNA fragment that is capable of being operably linked to the promoter. Techniques such as site-directed mutagenesis are also useful for modifying a heterologous nucleic acid.

A "subsequence" refers to a sequence of nucleic acids or amino acids that comprise a part of a longer sequence of nucleic acids or amino acids (e.g., polypeptide) respectively.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

The term "isolated" is meant to refer to material which is substantially or essentially free from components which normally accompany the material as found in its native state. Thus, an isolated material does not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least 60%, preferably 80%, most preferably 90–95% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et aL, eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J Mol. Biol.* 215: 403–410 and Altschuel et al. (1977) *Nucleic Acids Res.* 25: 3389–3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

The phrase "hybridizing specifically to", refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every polynucleotide sequence described herein which encodes a polypeptide also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a polypeptide is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of the fusion proteins and nucleic acid which encode the fusion proteins yield essentially identical products. For example, due to the degeneracy of the genetic code, "silent substitutions" (i.e., substitutions of a nucleic acid sequence which do not result in an alteration in an encoded polypeptide) are an implied feature of every nucleic acid sequence which encodes an amino acid. As described herein, sequences are preferably optimized for expression in a particular host cell used to produce the chimeric endonucleases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

DESCRIPTION OF THE PREFERRED EMBODIMENTS

The present invention provides fusion polypeptides that include a glycosyltransferase catalytic domain and at least one catalytic domain of one or more accessory enzymes. Accessory enzymes can, for example, catalyze a step in the formation of a nucleotide sugar which is a donor for the glycosyltransferase. Nucleic acids that encode the fusion polypeptides are also provided, as are expression vectors and host cells that include these nucleic acids.

The fusion polypeptides of the invention find use in the enzymatic synthesis of oligosaccharides. Significant advantages are provided by the fusion polypeptides. For example, the use of a fusion polypeptide that has two or more enzymatic activities reduces the number of polypeptides that must be obtained for a given synthesis. Thus, purification is simplified.

A. Glycosyltransferases

The fusion polypeptides of the invention include a catalytic domain of a glycosyltransferase. The catalytic domain can be from any of a wide variety of glycosyltransferases. Among the glycosyltransferases from one which one can obtain a catalytic domain are the sialyltransferases, N-acetylglucosaminyltransferases, N-acetylgalactosaminyltransferases, fucosyltransferases, galactosyltransferases, glucosyltransferases, xylosyltransferases, and mannosyltransferases.

The glycosyltransferases can be either prokaryotic or eukaryotic glycosyltransferases.

Eukaryotic Glycosyltransferases

The fusion polypeptides of the present invention can include a catalytic domain of a eukaryotic glycosyltransferase. Eukaryotic glycosyltransferases typically have topological domains at their amino terminus that are not required for catalytic activity (see, U.S. Pat. No. 5,032,519). The "cytoplasmic domain," which is most commonly between about 1 and about 10 amino acids in length, is the most amino-terminal domain. The adjacent domain, termed the "signal-anchor domain," is generally between about 10–26 amino acids in length. Adjacent to the signal-anchor domain is a "stem region," which is typically between about 20 and about 60 amino acids in length. The stem region functions as a retention signal to maintain the glycosyltransferase in the Golgi apparatus. The catalytic domain of the glycosyltransferase is found to the carboxyl side of the stem region.

In a presently preferred embodiment, the glycosyltransferase catalytic domains that are present in the fusion proteins of the invention substantially lack one or more of the cytoplasmic, signal-anchor, and stem region domains. More preferably, two of these domains are at least substantially absent from the fusion protein, and most preferably all three of the cytoplasmic domain, the signal-anchor domain, and the stem region are substantially or completely absent from the fusion proteins of the invention.

Many mammalian glycosyltransferases have been cloned and expressed and the recombinant proteins have been characterized in terms of donor and acceptor specificity and they have also been investigated through site directed mutagenesis in attempts to define residues involved in either donor or acceptor specificity (Aoki et al. (1990) *EMBO. J.* 9: 3171–3178; Harduin-Lepers et al. (1995) *Glycobiology* 5 (8): 741–758; Natsuka and Lowe (1994) *Current Opinion in Structural Biology* 4: 683–691; Zu et al. (1995) *Biochem. Biophys. Res. Comm.* 206 (1): 362–369; Seto et al. (1995) *Eur. J. Biochem.* 234: 323–328; Seto et al. (1997) *J. Biol. Chem.* 272: 14133–141388).

In some embodiments, the glycosyltransferase catalytic domain is obtained from a fucosyltransferase. A number of fucosyltransferases are known to those of skill in the art. Briefly, fucosyltransferases include any of those enzymes which transfer L-fucose from GDP-fucose to a hydroxy position of an acceptor sugar. In some embodiments, for example, the acceptor sugar is a GlcNAc in a Galβ(1→4) GlcNAc group in an oligosaccharide glycoside. Suitable fucosyltransferases for this reaction include the known Galβ (1→3,4)GlcNAc α(1→3,4)fucosyltransferase (FTIII, E.C. No. 2.4.1.65) which is obtained from human milk (see, Palcic, et al., *Carbohydrate Res.* 190:1–11 (1989); Prieels, et al., *J. Biol. Chem.* 256: 10456–10463 (1981); and Nunez, et al., *Can. J. Chem.* 59: 2086–2095 (1981)) and the Galβ (1→4)GlcNAc α(1→3)fucosyltransferases (FTIV, FTV, FTVI, and FTVII, E.C. No. 2.4.1.65) which are found in human serum. A recombinant form of Galβ(1→3,4)GlcNAc α(1→3,4)fucosyltransferase is also available (see, Dumas, et al., *Bioorg. Med. Letters* 1:425–428 (1991) and Kukowska-Latallo, et al., *Genes and Development* 4:1288–1303 (1990)). Other exemplary fucosyltransferases include α1,2 fucosyltransferase (E.C. No. 2.4.1.69). Enzymatic fucosylation can be carried out by the methods described in Mollicone, et al., *Eur. J. Biochem.* 191:169–176 (1990) or U.S. Pat. No. 5,374,655.

In another group of embodiments, the glycosyltransferase catalytic domain is obtained from a galactosyltransferase. Exemplary galactosyltransferases include α1,3-galactosyltransferases (E.C. No. 2.4.1.15 1, see, e.g., Dabkowski et al., *Transplant Proc.* 25:2921 (1993) and Yamamoto et al. *Nature* 345:229–233 (1990), bovine (GenBankj04989, Joziasse et al. (1989) *J. Biol. Chem.* 264:14290–14297), murine (GenBank m26925; Larsen et al. (1989) *Proc. Nat'l. Acad. Sci. USA* 86:8227–8231), porcine (GenBank L36152; Strahan et al (1995) *Immunogenetics* 41:101–105)). Another suitable α1,3-galactosyltransferase is that which is involved in synthesis of the blood group B antigen (EC 2.4.1.37, Yamamoto et al. (1990) *J. Biol. Chem.* 265:1146–1151 (human)). Also suitable for use in the fusion polypeptides of the invention are α1,4-galactosyltransferases, which include, for example, EC 2.4.1.90 (LacNAc synthetase) and EC 2.4.1.22 (lactose synthetase) (bovine (D'Agostaro et al (1989) *Eur. J. Biochem.* 183:211–217), human (Masri et al. (1988) *Biochem. Biophys. Res. Commun.* 157:657–663), murine (Nakazawa et al (1988) *J. Biochem.* 104:165–168), as well as E.C. 2.4.1.38 and the ceramide galactosyltransferase (EC 2.4.1.45, Stahl et al. (1994) *J. Neurosci. Res.* 38:234–242). Other suitable galactosyltransferases include, for example, α1,2-galactosyltransferases (from e.g., *Schizosaccharomyces pombe*, Chapell et al (1994) *Mol. Biol. Cell* 5:519–528).

Sialyltransferases are another type of glycosyltransferase that is useful in the recombinant cells and reaction mixtures of the invention. Examples of sialyltransferases that are suitable for use in the present invention include ST3Gal III preferably a rat ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al. (1996) *Glycobiology* 6: v–xiv). An exemplary α2,3-sialyltransferase (EC 2.4.99.6) transfers sialic acid to the non-reducing terminal Gal of a Galβ1→4GlcNAc disaccharide or glycoside. See, Van den Eijnden et al., *J. Biol. Chem.,* 256:3159 (1981), Weinstein et al., *J. Biol. Chem.,* 257:13845 (1982) and Wen et al., *J. Biol. Chem.,* 267:21011 (1992). Another exemplary α2,3-sialyltransferase (EC 2.4.99.4) transfers sialic acid to the non-reducing terminal Gal of a Galβ1→3GalNAc disaccharide or glycoside. See, Rearick et al., *J. Biol. Chem.,* 254: 4444 (1979) and Gillespie et al., *J. Biol. Chem.,* 267:21004 (1992). Further exemplary enzymes include Gal-β-1,4-GlcNAc α-2,6 sialyltransferase (See, Kurosawa et al. *Eur. J. Biochem.* 219: 375–381 (1994)). Sialyltransferase nomenclature is described in Tsuji, S. et al. (1996) *Glycobiology* 6:v–vii.

Other glycosyltransferases that can used in the fusion polypeptides of the invention have been described in detail, as for the sialyltransferases, galactosyltransferases, and fucosyltransferases. In particular, the glycosyltransferase can also be, for instance, glucosyltransferases, e.g., Alg8 (Stagljov et al., *Proc. Natl. Acad. Sci. USA* 91:5977 (1994)) or Alg5 (Heesen et al. *Eur. J. Biochem.* 224:71 (1994)), N-acetylgalactosaminyltransferases such as, for example, β(1,3)-N-acetylgalactosaminyltransferase, β(1,4)-N-acetylgalactosaminyltransferases (U.S. Pat. No. 5,691,180, Nagata et al. *J. Biol. Chem.* 267:12082–12089 (1992), and Smith et al. *J. Biol Chem.* 269:15162 (1994)) and polypeptide N-acetylgalactosaminyltransferase (Homa et al. *J. Biol Chem.* 268:12609 (1993)). Suitable N-acetylglucosaminyltransferases include GnTI (2.4.1.101, Hull et al., BBRC 176:608 (1991)), GnTII, and GnTIII (Ihara et al. *J. Biochem.* 113:692 (1993)), GnTV (Shoreiban et al. *J. Biol. Chem.* 268: 15381 (1993)), O-linked N-acetylglucosaminyltransferase (Bierhuizen et al. *Proc. Natl. Acad. Sci. USA* 89:9326 (1992)), N-acetylglucosamine-1-phosphate transferase (Rajput et al. *Biochem J.* 285:985 (1992), and hyaluronan synthase. Also of interest are enzymes involved in proteoglycan synthesis, such as, for example, N-acetylgalactosaminyltransferase I (EC 2.4.1.174), and enzymes involved in chondroitin sulfate synthesis, such as N-acetylgalactosaminyltransferase II (EC 2.4.1.175). Suitable mannosyltransferases include α(1,2) mannosyltransferase, α(1, 3) mannosyltransferase, β(1,4) mannosyltransferase, Dol-P-Man synthase, OCh1, and Pmt1. Xylosyltransferases include, for example, protein xylosyltransferase (EC 2.4.2.26).

Prokaryotic Glycosyltransferases

In other embodiments, the fusion proteins of the invention include a glycosyltransferase catalytic domain from a prokaryotic glycosyltransferase. Nucleic acids encoding several prokaryotic glycosyltransferases have been cloned and characterized, and can be used in the fusion proteins of the invention. As is the case for eukaryotic glycosyltransferases, prokaryotic glycosyltransferases often have a membrane-spanning domain near the amino terminus that can be omitted, if desired, from the fusion polypeptide.

Suitable prokaryotic glycosyltransferases include enzymes involved in synthesis of lipooligosaccharides (LOS), which are produced by many Gram negative bacteria. The LOS typically have terminal glycan sequences that mimic glycoconjugates found on the surface of human epithelial cells or in host secretions (Preston et al. (1996) *Critical Reviews in Microbiology* 23 (3): 139–180). Such enzymes include, but are not limited to, the proteins of the rfa operons of species such as *E. coli* and *Salmonella typhimurium*, which include a α1,6-galactosyltransferase and a α1,3-galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an α1,2-glucosyltransferase (rfaJ)(Swiss-Prot Accession No. P27129 (*E. coli*) and Swiss-Prot Accession No. P19817 (*S. typhimurium*)), and an α1,2-N-acetylglucosaminyltransferase (rfaK)(EMBL Accession No. U00039 (*E. coli*). Other glycosyltransferases for which amino acid and/or nucleic acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the fusion proteins of the invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al. (1994) *J. Med. Microbiol.* 41: 236–243). The genes from *N. meningitidis* and *N. gonorrhoeae* that encode the glycosyltransferases involved in the biosynthesis of these structures have been identified from *N. meningitidis* immunotypes L3 and L1 (Jennings et al. (1995) *Mol. Microbiol.* 18: 729–740) and the *N. gonorrhoeae* mutant F62 (Gotshlich (1994) *J. Exp. Med.* 180: 2181–2190). In *N. meningitidis*, a locus consisting of 3 genes, lgtA, lgtB and lg E, encodes the glycosyltransferase enzymes required for addition of the last three of the sugars in the lacto-N-neotetraose chain (Wakarchuk et al. (1996) *J. Biol. Chem.* 271: 19166–73). Recently the enzymatic activity of the lgtB and lgtA gene product was demonstrated, providing the first direct evidence for their proposed glycosyltransferase function (Wakarchuk et al. (1996) *J. Biol. Chem.* 271 (45): 28271–276). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al. (1995), supra.). *Neisseria* glycosyltransferases and associated genes are also described in U.S. Pat. No. 5,545,553 (Gotshlich). An α1,3-fucosyltransferase gene from *Helicobacter pylori* has also been characterized (Martin et al. (1997) *J. Biol. Chem.* 272: 21349–21356).

Sialyltransferases from prokaryotes have been described by, for example, Weisgerber et al. (1991) *Glycobiol.* 1:357–365; Frosch, M. et al. (1991) *Mol. Microbiol.* 5:1251–1263; and Gilbert, M. et al. (1996) *J. Biol. Chem.* 271:28271–28276. It has been suggested that the bacterial sialyltransferases might have a wider spectrum of acceptors than their mammalian counterparts (Kajihara, Y. et al. (1996) *J. Org. Chem.* 61:8632–8635 and Gilbert et al., *Eur. J. Biochem.* 249: 187–194 (1997)).

As is the case for eukaryotic glycosyltransferases, one can readily obtain nucleic acids that encode other prokaryotic glycosyltransferases that can be used in constructing fusion polypeptides according to the invention.

B. Accessory Enzymes Involved in Nucleotide Sugar Formation

The fusion polypeptides of the invention include, in addition to the glycosyltransferase catalytic domain(s), at least one catalytic domain from an accessory enzyme. Accessory enzymes include, for example, those enzymes that are involved in the formation of a nucleotide sugar. The accessory enzyme can be involved in attaching the sugar to a nucleotide, or can be involved in making the sugar or the nucleotide, for example. The nucleotide sugar is generally one that is utilized as a saccharide donor by the glycosyltransferase catalytic domain of the particular fusion polypeptide. Examples of nucleotide sugars that are used as sugar donors by glycosyltransferases include, for example, GDP-Man, UDP-Glc, UDP-Gal, UDP-GlcNAc, UDP-GalNAc, CMP-sialic acid, UDP-xylose, GDP-Fuc, GDP-GlcNAc, among others.

Accessory enzymes that are involved in synthesis of nucleotide sugars are well known to those of skill in the art. For a review of bacterial polysaccharide synthesis and gene nomenclature, see, e.g., Reeves et al., *Trends Microbiol.* 4: 495–503 (1996). The methods described above for obtaining glycosyltransferase-encoding nucleic acids are also applicable to obtaining nucleic acids that encode enzymes involved in the formation of nucleotide sugars. For example, one can use one of nucleic acids known in the art, some of which are listed below, directly or as a probe to isolate a corresponding nucleic acid from other organisms of interest.

As one example, to produce a galactosylated soluble oligosaccharide, a galactosyltransferase is often used. However, galactosyltransferases generally use as a galactose donor the activated nucleotide sugar UDP-Gal, which is comparatively expensive. To reduce the expense of the reaction, one can construct one or more fusion polypeptides that have the galactosyltransferase catalytic domain and also a catalytic domain from one of the accessory enzymes that are involved in the biosynthetic pathway which leads to UDP-Gal. For example, glucokinase (EC 2.7.1.12) catalyzes the phosphorylation of glucose to form Glc-6-P. Genes that encode glucokinase have been characterized (e.g., *E. coli*: GenBank AE000497 U00096, Blattner et al., *Science* 277: 1453–1474 (1997); *Bacillus subtilis*: GenBank Z99124, AL009126, Kunst et al., *Nature* 390, 249–256 (1997)), and thus can be readily obtained from many organisms by, for example, hybridization or amplification. A fusion polypeptide that contains a catalytic domain from this enzyme, as well as those of the subsequent enzymes in the pathway as set forth below, will thus be able to form UDP-glucose from readily available glucose, which can be either produced by the organism or added to the reaction mixture.

The next step in the pathway leading to UDP-Gal is catalyzed by phosphoglucomutase (EC 5.4.2.2), which converts Glc-6-P to Glc-1-P. Again, genes encoding this enzyme have been characterized for a wide range of organisms (e.g.,

*Agrobacterium tumefaciens*: GenBank AF033856, Uttaro et al. *Gene* 150: 117–122 (1994) [published erratum appears in *Gene* (1995) 155:141–3]; *Entamoeba histolytica*: GenBank Y14444, Ortner et al., *Mol. Biochem. Parasitol.* 90, 121–129 (1997); *Mesembryanthemum crystallinum*: GenBank U84888; *S. cerevisiae*: GenBank X72016, U09499, X74823, Boles et al., *Eur. J. Biochem.* 220: 83–96 (1994), Fu et al., *J. Bacteriol.* 177 (11), 3087–3094 (1995); human: GenBank M83088 (PGM1), Whitehouse et al., *Proc. Nat'l. Acad. Sci. U.S.A.* 89: 411–415 (1992), *Xanthomonas campestris*: GenBank M83231, Koeplin et al., *J. Bacteriol.* 174: 191–199 (1992); *Acetobacter xylinum*: GenBank L24077, Brautaset et al., *Microbiology* 140 (Pt 5), 1183–1188 (1994); *Neisseria meningitidis*: GenBank U02490, Zhou et al., *J. Biol. Chem.* 269 (15), 11162–11169 (1994).

UDP-glucose pyrophosphorylase (EC 2.7.7.9) catalyzes the next step in the pathway, conversion of Glc-1-P to UDP-Glc. Genes encoding UDP-Glc pyrophosphorylase are described for many organisms (e.g., *E. coli*: GenBank M98830, Weissborn et al., *J. Bacteriol.* 176: 2611–2618 (1994); *Cricetulus griseus*: GenBank AF004368, Flores-Diaz et al., *J. Biol. Chem.* 272: 23784–23791 (1997); *Acetobacter xylinum*: GenBank M76548, Brede et al., *J. Bacteriol.* 173, 7042–7045 (1991); *Pseudomonas aeruginosa* (galU): GenBank AJ010734, U03751; *Streptococcus pneumoniae*: GenBank AJ004869; *Bacillus subtilis*: GenBank Z22516, L12272; Soldo et al., *J. Gen. Microbiol.* 139 (Pt 12), 3185–3195 (1993); *Solanum tuberosum*: GenBank U20345, L77092, L77094, L77095, L77096, L77098, U59182, Katsube et al., *J. Biochem.* 108: 321–326 (1990); *Hordeum vulgare* (barley): GenBank X91347; *Shigella flexneri*: GenBank L32811, Sandlin et al., *Infect. Immun.* 63: 229–237 (1995); human: GenBank U27460, Duggleby et al., *Eur. J. Biochem.* 235 (1–2), 173–179 (1996); bovine: GenBank L14019, Konishi et al., *J. Biochem.* 114, 61–68 (1993).

Finally, UDP-Glc 4'-epimerase (UDP-Gal 4' epimerase; EC 5.1.3.2) catalyzes the conversion of UDP-Glc to UDP-Gal. The *Streptococcus thermophilus* UDPgalactose 4-epimerase gene described by Poolman et al. (*J. Bacteriol* 172: 4037–4047 (1990)) is a particular example of a gene that is useful in the present invention. Exemplary genes encoding UDPglucose 4-epimerase include those of *E. coli, K. pneumoniae, S. lividans,* and *E. stewartii*, as well as *Salmonella* and *Streptococcus* species. Nucleotide sequences are known for UDP-Glc 4'-epimerases from several organisms, including *Pasteurella haemolytica*, GenBank U39043, Potter et al., *Infect. Immun.* 64 (3), 855–860 (1996); *Yersinia enterocolitica*, GenBank Z47767, X63827, Skurnik et al., *Mol. Microbiol.* 17: 575–594 (1995); *Cyamopsis tetragonoloba*: GenBank AJ005082; *Pachysolen tannophilus*: GenBank X68593, Skrzypek et al., *Gene* 140 (1), 127–129 (1994); *Azospirillum brasilense*: GenBank Z25478, De Troch et al., *Gene* 144 (1), 143–144 (1994); *Arabidopsis thaliana*: GenBank Z54214, Dormann et al., *Arch. Biochem. Biophys.* 327: 27–34 (1996); *Bacillus subtilis*: GenBank X99339, Schrogel et al., *FEMS Microbiol. Lett.* 145: 341–348 (1996); *Rhizobium meliloti*: GenBank X58126 S81948, Buendia et al., *Mol. Biol.* 5: 1519–1530 (1991); *Rhizobium leguminosarum*: GenBank X96507; *Erwinia amylovora*: GenBank X76172, Metzger et al., *J Bacteriol.* 176: 450–459 (1994); *S. cerevisiae*: GenBank X81324 (cluster of epimerase and UDP-glucose pyrophosphorylase), Schaaff-Gerstenschlager, *Yeast* 11: 79–83 (1995); *Neisseria meningitidis*: GenBank U19895, L20495, Lee et al., *Infect. Immun.* 63: 2508–2515 (1995), Jennings et al., *Mol. Microbiol.* 10: 361–369 (1993); and *Pisum sativum*: GenBank U31544.

Often, genes encoding enzymes that make up a pathway involved in synthesizing nucleotide sugars are found in a single operon or region of chromosomal DNA. For example, the *Xanthomonas campestris* phosphoglucomutase, phosphomannomutase, (xanA), phosphomannose isomerase, and GDP-mannose pyrophosphorylase (xanB) genes are found on a single contiguous nucleic acid fragment (Koeplin et al., *J. Bacteriol.* 174, 191–199 (1992)). *Klebsiella pneumoniae* galactokinase, galactose-1-phosphate uridyltransferase, and UDP-galactose 4'-epimerase are also found in a single operon (Peng et al. (1992) *J. Biochem.* 112: 604–608). Many other examples are described in the references cited herein.

An alternative galactosyltransferase fusion polypeptide can include a catalytic domain from UDP-Gal pyrophosphorylase (galactose-1-phosphate uridyltransferase), which converts Gal-1-P to UDP-Gal. Genes that encode UDP-Gal pyrophosphorylase have been characterized for several organisms, including, for example, *Rattus norvegicus*: GenBank L05541, Heidenreich et al., *DNA Seq.* 3: 311–318 (1993); *Lactobacillus casei*: GenBank AF005933 (cluster of galactokinase (galK), UDP-galactose 4-epimerase (galE), galactose 1-phosphate-uridyltransferase (galT)), Bettenbrock et al., *Appl. Environ. Microbiol.* 64: 2013–2019 (1998); *E. coli*: GenBank X06226 (galE and galT for UDP-galactose-4-epimerase and galactose-1-P uridyltransferase), Lemaire et al., *Nucleic Acids Res.* 14: 7705–7711 (1986)); *B. subtilis*: GenBank Z99123 AL009126; *Neisseria gonorrhoeae*: GenBank Z50023, Ullrich et al., *J. Bacteriol.* 177: 6902–6909 (1995); *Haemophilus influenzae*: GenBank X65934 (cluster of galactose-1-phosphate uridyltransferase, galactokinase, mutarotase and galactose repressor), Maskell et al., *Mol. Microbiol.* 6: 3051–3063 (1992), GenBank M12348 and M12999, Tajima et al., *Yeast* 1: 67–77 (1985)); *S. cerevisiae*: GenBank X81324, Schaaff-Gerstenschlager et al., *Yeast* 11: 79–83 (1995); *Mus musculus*: GenBank U41282; human: GenBank M96264, M18731, Leslie et al., *Genomics* 14: 474–480 (1992), Reichardt et al., *Mol. Biol. Med.* 5: 107–122 (1988); *Streptomyces lividans*: M18953 (galactose 1-phosphate uridyltransferase, UDP-galactose 4-epimerase, and galactokinase), Adams et al., *J. Bacteriol.* 170: 203–212 (1988).

Catalytic domains of UDP-GlcNAc 4' epimerase (UDP-GalNAc 4'-epimerase)(EC 5.1.3.7), which catalyzes the conversion of UDP-GlcNAc to UDP-GalNAc, and the reverse reaction, are also suitable for use in the fusion polypeptides of the invention. Several loci that encode this enzyme are described above. See also, U.S. Pat. No. 5,516,665.

Another example of a fusion polypeptide provided by the invention is used for producing a fucosylated soluble oligosaccharide. The donor nucleotide sugar for fucosyltransferases is GDP-fucose, which is relatively expensive to produce. To reduce the cost of producing the fucosylated oligosaccharide, the invention provides fusion polypeptides that can convert the relatively inexpensive GDP-mannose into GDP-fucose, and then catalyze the transfer of the fucose to an acceptor saccharide. These fusion polypeptides include a catalytic domain from at least one of a GDP-mannose dehydratase, a GDP-4-keto-6-deoxy-D-mannose 3,5-epimerase, or a GDP-4-keto-6-deoxy-L-glucose 4-reductase. When each of these enzyme activities is provided, one can convert GDP-mannose into GDP-fucose.

The nucleotide sequence of an *E. coli* gene cluster that encodes GDP-fucose-synthesizing enzymes is described by Stevenson et al. (1996) *J. Bacteriol.* 178: 4885–4893; GenBank Accession No. U38473). This gene cluster had been reported to include an open reading frame for GDP-mannose dehydratase (nucleotides 8633–9754; Stevenson et al., supra.). It was recently discovered that this gene cluster also contains an open reading frame that encodes an enzyme that has both 3,5 epimerization and 4-reductase activities (see, commonly assigned U.S. Provisional Patent Application No. 60/071,076, filed Jan. 15, 1998), and thus is capable of converting the product of the GDP-mannose dehydratase reaction (GDP-4-keto-6-deoxymannose) to GDP-fucose. This ORF, which is designated YEF B, is found between nucleotides 9757–10722. Prior to this discovery that YEF B encodes an enzyme having two activities, it was not known whether one or two enzymes were required for conversion of GDP-4-keto-6-deoxymannose to GDP-fucose. The nucleotide sequence of a gene encoding the human Fx enzyme is found in GenBank Accession No. U58766.

Also provided are fusion polypeptides that include a mannosyltransferase catalytic domain and a catalytic domain of a GDP-Man pyrophosphorylase (EC 2.7.7.22), which converts Man-1-P to GDP-Man. Suitable genes are known from many organisms, including *E. coli*: GenBank U13629, AB010294, D43637 D13231, Bastin et al., *Gene* 164: 17–23 (1995), Sugiyama et al., *J. Bacteriol.* 180: 2775–2778 (1998), Sugiyama et al., *Microbiology* 140 (Pt 1): 59–71 (1994), Kido et al., *J. Bacteriol.* 177: 2178–2187 (1995); *Klebsiella pneumoniae*: GenBank AB010296, AB010295, Sugiyama et al., *J. Bacteriol.* 180: 2775–2778 (1998); *Salmonella enterica*: GenBank X56793 M29713, Stevenson et al., *J. Bacteriol.* 178: 4885–4893 (1996).

The fusion polypeptides of the invention for fucosylating a saccharide acceptor can also utilize enzymes that provide a minor or "scavenge" pathway for GDP-fucose formation. In this pathway, free fucose is phosphorylated by fucokinase to form fucose 1-phosphate, which, along with guanosine 5'-triphosphate (GTP), is used by GDP-fucose pyrophosphorylase to form GDP-fucose (Ginsburg et al., *J. Biol. Chem.*, 236: 2389–2393 (1961) and Reitman, *J. Biol. Chem.*, 255: 9900–9906 (1980)). Accordingly, a fucosyltransferase catalytic domain can be linked to a catalytic domain from a GDP-fucose pyrophosphorylase, for which suitable nucleic acids are described in copending, commonly assigned U.S. patent application Ser. No. 08/826,964, filed Apr. 9, 1997. Fucokinase-encoding nucleic acids are described for, e.g., *Haemophilus influenzae* (Fleischmann et al. (1995) *Science* 269:496–512) and *E. coli* (Lu and Lin (1989) *Nucleic Acids Res.* 17: 4883–4884).

Other pyrophosphorylases are known that convert a sugar phosphate into a nucleotide sugar. For example, UDP-GalNAc pyrophosphorylase catalyzes the conversion of GalNAc to UDP-GalNac. UDP-GlcNAc pyrophosphorylase (EC 2.7.7.23) converts GlcNAc-1-P to UDP-GlcNAc (*B. subtilis*: GenBank Z99104 AL009126, Kunst et al., supra.; *Candida albicans*: GenBank AB011003, Mio et al., *J. Biol. Chem.* 273 (23), 14392–14397 (1998); *Saccharomyces cerevisiae*: GenBank AB011272, Mio et al., supra.; human: GenBank AB011004, Mio et al., supra.). These can also be used in the fusion polypeptides of the invention.

The invention also provides fusion polypeptides that are useful for sialylation reactions. These fusion polypeptides include a catalytic domain from a sialyltransferase and a catalytic domain from a CMP-sialic acid synthetase (EC 2.7.7.43, CMP-N-acetylneuraminic acid synthetase). Such genes are available from, for example, *Mus musculus* (GenBank AJ006215, Munster et al., *Proc. Natl. Acad. Sci. U.S.A.* 95: 9140–9145 (1998)), rat (Rodriguez-Aparicio et al. (1992) *J. Biol. Chem.* 267: 9257–63), *Haemophilus ducreyi* (Tullius et al. (1996) *J. Biol. Chem.* 271: 15373–80), *Neisseria meningitidis* (Ganguli et al. (1994) *J. Bacteriol.* 176: 4583–9), group B streptococci (Haft et al. (1994) *J. Bacteriol.* 176: 7372–4), and *E. coli* (GenBank J05023, Zapata et al. (1989) *J. Biol. Chem.* 264: 14769–14774). Alternatively, fusion proteins for sialylation reactions can have a catalytic domain from either or both of GlcNAc 2' epimerase (EC 5.1.3.8), which converts GlcNAc to ManNAc, and neuraminic acid aldolase (EC 4.1.3.3; SwissProt Accession No. P06995), which in turn converts the ManNAc to sialic acid.

Additional accessory enzymes from which one can obtain a catalytic domain are those that are involved in forming reactants consumed in a glycosyltransferase cycle. For example, any of several phosphate kinases are useful as accessory enzymes. Polyphosphate kinase (EC 2.7.4.1), for example, catalyzes the formation of ATP; nucleoside phosphate kinases (EC 2.7.4.4) can form the respective nucleoside diphosphates; creatine phosphate kinase (EC 2.7.3.2); myokinase (EC 2.7.4.3); N-acetylglucosamine acetyl kinase (EC 2.7.1.59); acetyl phosphate kinase; and pyruvate kinase (EC 2.7.1.40).

C. Cloning of Glycosyltransferase and Accessory Enzyme Nucleic Acids

Nucleic acids that encode glycosyltransferases and accessory enzymes, and methods of obtaining such nucleic acids, are known to those of skill in the art. Suitable nucleic acids (e.g., cDNA, genomic, or subsequences (probes)) can be cloned, or amplified by in vitro methods such as the polymerase chain reaction (PCR), the ligase chain reaction (LCR), the transcription-based amplification system (TAS), the self-sustained sequence replication system (SSR). A wide variety of cloning and in vitro amplification methodologies are well-known to persons of skill. Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning-A Laboratory Manual* (2nd ed.) Vol. 1–3, Cold Spring Harbor Laboratory, Cold Spring Harbor Press, NY, (Sambrook et al.); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

DNA that encodes glycosyltransferase and accessory enzyme polypeptides, or subsequences thereof, can be prepared by any suitable method described above, including, for example, cloning and restriction of appropriate sequences. In one preferred embodiment, a nucleic acid encoding a glycosyltransferase or accessory enzyme can be isolated by routine cloning methods. A nucleotide sequence of a glycosyltransferase or accessory enzyme as provided in, for example, GenBank or other sequence database (see above) can be used to provide probes that specifically hybridize to a glycosyltransferase or accessory enzyme gene in a genomic DNA sample, or to a glycosyltransferase or accessory enzyme mRNA in a total RNA sample (e.g., in a Southern or Northern blot). Once the target glycosyltransferase or accessory enzyme nucleic acid is identified, it can be isolated according to standard methods known to those of skill in the art (see, e.g., Sambrook et al. (1989) *Molecular Cloning: A Laboratory Manual,* 2nd Ed., Vols. 1–3, Cold Spring Harbor Laboratory; Berger and Kimmel (1987) *Methods in Enzymology, Vol. 152: Guide to Molecular Cloning Techniques*, San Diego: Academic Press, Inc.; or Ausubel et al. (1987) *Current Protocols in Molecular Biology*, Greene Publishing and Wiley-Interscience, New York).

Alternatively, subsequences can be cloned and the appropriate subsequences cleaved using appropriate restriction enzymes. The fragments may then be ligated to produce the desired DNA sequence.

A glycosyltransferase nucleic acid can also be cloned by detecting its expressed product by means of assays based on the physical, chemical, or immunological properties. For example, one can identify a cloned glycosyltransferase nucleic acid by the ability of a polypeptide encoded by the nucleic acid to catalyze the transfer of a monosaccharide from a donor to an acceptor moiety. In a preferred method, capillary electrophoresis is employed to detect the reaction products. This highly sensitive assay involves using either monosaccharide or disaccharide aminophenyl derivatives which are labeled with fluorescein as described in Wakarchuk et al. (1996) *J. Biol. Chem.* 271 (45): 28271–276. For example, to assay for a *Neisseria* lgtC enzyme, either FCHASE-AP-Lac or FCHASE-AP-Gal can be used, whereas for the *Neisseria* lgtB enzyme an appropriate reagent is FCHASE-AP-GlcNAc (Id.).

As an alternative to cloning a glycosyltransferase or accessory enzyme gene or cDNA, a glycosyltransferase nucleic acid can be chemically synthesized from a known sequence that encodes a glycosyltransferase. Suitable methods include the phosphotriester method of Narang et al. (1979) *Meth. Enzymol.* 68: 90–99; the phosphodiester method of Brown et al. (1979) *Meth. Enzymol.* 68: 109–151; the diethylphosphoramidite method of Beaucage et al. (1981) *Tetra. Lett.*, 22: 1859–1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences.

Glycosyltransferase and accessory enzyme nucleic acids can be cloned using DNA amplification methods such as polymerase chain reaction (PCR). Thus, for example, the nucleic acid sequence or subsequence is PCR amplified, using a sense primer containing one restriction site (e.g., NdeI) and an antisense primer containing another restriction site (e.g., HindIII). This will produce a nucleic acid encoding the desired glycosyltransferase or accessory enzyme sequence or subsequence and having terminal restriction sites. This nucleic acid can then be easily ligated into a vector containing a nucleic acid encoding the second molecule and having the appropriate corresponding restriction sites. Suitable PCR primers can be determined by one of skill in the art using the sequence information provided in GenBank or other sources. Appropriate restriction sites can also be added to the nucleic acid encoding the glycosyltransferase protein or protein subsequence by site-directed mutagenesis. The plasmid containing the glycosyltransferase-encoding nucleotide sequence or subsequence is cleaved with the appropriate restriction endonuclease and then ligated into an appropriate vector for amplification and/or expression according to standard methods. Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) C&EN 36–47; *The Journal Of NIH Research* (1991) 3: 81–94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077–1080; Van Brunt (1990) *Biotechnology* 8: 291–294; Wu and Wallace (1989) *Gene* 4: 560; and Barringer et al. (1990) *Gene* 89: 117.

Other physical properties of a polypeptide expressed from a particular nucleic acid can be compared to properties of known glycosyltransferases or accessory enzymes to provide another method of identifying suitable nucleic acids. Alternatively, a putative glycosyltransferase or accessory enzyme gene can be mutated, and its role as a glycosyltransferase or accessory enzyme established by detecting a variation in the structure of an oligosaccharide normally produced by the glycosyltransferase or accessory enzyme.

In some embodiments, it may be desirable to modify the glycosyltransferase and/or accessory enzyme nucleic acids. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81–97, Roberts et al. (1987) *Nature* 328: 731–734.

For example, the glycosyltransferase and/or accessory enzyme nucleic acids can be modified to facilitate the linkage of the two domains to obtain the polynucleotides that encode the fusion polypeptides of the invention. Glycosyltransferase catalytic domains and accessory enzyme catalytic domains that are modified by such methods are also part of the invention. For example, codon for a cysteine residue can be placed at either end of a domain so that the domain can be linked by, for example, a sulfide linkage. The modification can be done using either recombinant or chemical methods (see, e.g., Pierce Chemical Co. catalog, Rockford Ill.). The glycosyltransferase and/or accessory enzyme catalytic domains are typically joined by linker domains, which are typically polypeptide sequences, such as poly glycine sequences of between about 5 and 200 amino acids, with between about 10–100 amino acids being typical. In some embodiments, proline residues are incorporated into the linker to prevent the formation of significant secondary structural elements by the linker. Preferred linkers are often flexible amino acid subsequences which are synthesized as part of a recombinant fusion protein. In one embodiment, the flexible linker is an amino acid subsequence comprising a proline such as Gly(x)-Pro-Gly(x) where x is a number between about 3 and about 100. In other embodiments, a chemical linker is used to connect synthetically or recombinantly produced glycosyltransferase and accessory enzyme catalytic domains. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

In a preferred embodiment, the recombinant nucleic acids present in the cells of the invention are modified to provide preferred codons which enhance translation of the nucleic acid in a selected organism (e.g., yeast preferred codons are substituted into a coding nucleic acid for expression in yeast).

D. Expression Cassettes and Host Cells for Expressing the Fusion Polypeptides Typically, the polynucleotide that encodes the fusion polypeptide is placed under the control of a promoter that is functional in the desired host cell. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion polypeptides are incorporated for high level expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21–25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of fusion polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*.

A ribosome binding site (RBS) is conveniently included in the expression cassettes of the invention. An RBS in *E. coli*, for example, consists of a nucleotide sequence 3–9 nucleotides in length located 3–11 nucleotides upstream of the initiation codon (Shine and Dalgarno, *Nature* (1975) 254: 34; Steitz, *In Biological regulation and development: Gene expression* (ed. R. F. Goldberger), vol. 1, p. 349, 1979, Plenum Publishing, NY).

For expression of the fusion polypeptides in yeast, convenient promoters include GAL1-10 (Johnson and Davies (1984) *Mol. Cell. Biol.* 4:1440–1448) ADH2 (Russell et al. (1983) *J. Biol. Chem.* 258:2674–2682), PHO5 (*EMBO J.* (1982) 6:675–680), and MFα (Herskowitz and Oshima (1982) in *The Molecular Biology of the Yeast Saccharomyces* (eds. Strathem, Jones, and Broach) Cold Spring Harbor Lab., Cold Spring Harbor, N.Y., pp. 181–209). Another suitable promoter for use in yeast is the ADH2/GAPDH hybrid promoter as described in Cousens et al., *Gene* 61:265–275 (1987). For filamentous fungi such as, for example, strains of the fungi *Aspergillus* (McKnight et al., U.S. Pat. No. 4,935,349), examples of useful promoters include those derived from *Aspergillus nidulans* glycolytic genes, such as the ADH3 promoter (McKnight et al., *EMBO J.* 4: 2093 2099 (1985)) and the tpiA promoter. An example of a suitable terminator is the ADH3 terminator (McKnight et al.).

Suitable constitutive promoters for use in plants include, for example, the cauliflower mosaic virus (CaMV) 35S transcription initiation region and region VI promoters, the 1'- or 2'- promoter derived from T-DNA of *Agrobacterium tumefaciens*, and other promoters active in plant cells that are known to those of skill in the art. Other suitable promoters include the full-length transcript promoter from Figwort mosaic virus, actin promoters, histone promoters, tubulin promoters, or the mannopine synthase promoter (MAS). Other constitutive plant promoters include various ubiquitin or polyubiquitin promoters derived from, inter alia, *Arabidopsis* (Sun and Callis, *Plant J.*, 11 (5):1017–1027 (1997)), the mas, Mac or DoubleMac promoters (described in U.S. Pat. No. 5,106,739 and by Comai et al., *Plant Mol. Biol.* 15:373–381 (1990)) and other transcription initiation regions from various plant genes known to those of skill in the art. Such genes include for example, ACT11 from *Arabidopsis* (Huang et al., *Plant Mol. Biol.* 33:125–139 (1996)), Cat3 from *Arabidopsis* (GenBank No. U43147, Zhong et al, *Mol. Gen. Genet.* 251:196–203 (1996)), the gene encoding stearoyl-acyl carrier protein desaturase from *Brassica napus* (Genbank No. X74782, Solocombe et al., *Plant Physiol.* 104:1167–1176 (1994)), GPc1 from maize (GenBank No. X15596, Martinez et al., *J. Mol. Biol* 208: 551–565 (1989)), and Gpc2 from maize (GenBank No. U45855, Manjunath et al., *Plant Mol. Biol.* 33:97–112 (1997)). Useful promoters for plants also include those obtained from Ti- or Ri-plasmids, from plant cells, plant viruses or other hosts where the promoters are found to be functional in plants. Bacterial promoters that function in plants, and thus are suitable for use in the methods of the invention include the octopine synthetase promoter, the nopaline synthase promoter, and the manopine synthetase promoter. Suitable endogenous plant promoters include the ribulose-1,6-biphosphate (RUBP) carboxylase small subunit (ssu) promoter, the (α-conglycinin promoter, the phaseolin promoter, the ADH promoter, and heat-shock promoters.

Either constitutive or regulated promoters can be used in the present invention. Regulated promoters can be advantageous because the host cells can be grown to high densities before expression of the fusion polypeptides is induced. High level expression of heterologous proteins slows cell growth in some situations. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074–8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No.

WO98/20111, provides a level of expression that is greater than that provided by either promoter alone.

Inducible promoters for use in plants are known to those of skill in the art (see, e.g., references cited in Kuhlemeier et al (1987) *Ann. Rev. Plant Physiol.* 38:221), and include those of the 1,5-ribulose bisphosphate carboxylase small subunit genes of *Arabidopsis thaliana* (the "ssu" promoter), which are light-inducible and active only in photosynthetic tissue, anther-specific promoters (EP 344029), and seed-specific promoters of, for example, *Arabidopsis thaliana* (Krebbers et al. (1988) *Plant Physiol.* 87:859).

Inducible promoters for other organisms are also well known to those of skill in the art. These include, for example, the arabinose promoter, the lacZ promoter, the metallothionein promoter, and the heat shock promoter, as well as many others.

A construct that includes a polynucleotide of interest operably linked to gene expression control signals that, when placed in an appropriate host cell, drive expression of the polynucleotide is termed an "expression cassette." Expression cassettes that encode the fusion polypeptides of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. N0. WO98/20111.

The construction of polynucleotide constructs generally requires the use of vectors able to replicate in bacteria. A plethora of kits are commercially available for the purification of plasmids from bacteria. For their proper use, follow the manufacturer's instructions (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in *Streptomyces* or *Bacillus* is also possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for *Bacilli*. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al, supra. A preferred selectable marker for use in bacterial cells is a kanamycin resistance marker (Vieira and Messing, *Gene* 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Suitable selectable markers for use in mammalian cells include, for example, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg (1981) *Proc. Nat'l. Acad. Sci. USA* 78: 2072; Southern & Berg (1982) *J. Mol. Appl. Genet.* 1: 327).

Selection markers for plant and/or other eukaryotic cells often confer resistance to a biocide or an antibiotic, such as, for example, kanamycin, G 418, bleomycin, hygromycin, or chloramphenicol, or herbicide resistance, such as resistance to chlorsulfuron or Basta. Examples of suitable coding sequences for selectable markers are: the neo gene which codes for the enzyme neomycin phosphotransferase which confers resistance to the antibiotic kanamycin (Beck et al (1982) *Gene* 19:327); the hyg gene, which codes for the enzyme hygromycin phosphotransferase and confers resistance to the antibiotic hygromycin (Gritz and Davies (1983) *Gene* 25:179); and the bar gene (EP 242236) that codes for phosphinothricin acetyl transferase which confers resistance to the herbicidal compounds phosphinothricin and bialaphos.

Construction of suitable vectors containing one or more of the above listed components employs standard ligation techniques as described in the references cited above. Isolated plasmids or DNA fragments are cleaved, tailored, and re-ligated in the form desired to generate the plasmids required. To confirm correct sequences in plasmids constructed, the plasmids can be analyzed by standard techniques such as by restriction endonuclease digestion, and/or sequencing according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors. In yeast, vectors include Yeast Integrating plasmids (e.g., YIp5) and Yeast Replicating plasmids (the YRp series plasmids) and pGPD-2. Expression in mammalian cells can be achieved using a variety of commonly available plasmids, including pSV2, pBC12BI, and p91023, as well as lytic virus vectors (e.g., *vaccinia* virus, adeno virus, and baculovirus), episomal virus vectors (e.g., bovine papillomavirus), and retroviral vectors (e.g., murine retroviruses).

The methods for introducing the expression vectors into a chosen host cell are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297–16302.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). In embodiments in which the fusion polypeptides are secreted from the cell, either into the periplasm or into the extracellular medium, the DNA sequence is linked to a cleavable signal peptide sequence. The signal sequence directs translocation of the fusion polypeptide through the cell membrane. An example of a suitable vector for use in *E. coli* that contains a promoter-signal sequence unit is pTA1529, which has the *E. coli* phoA promoter and signal sequence (see, e.g., Sambrook et al., supra.; Oka et al., *Proc. Natl. Acad. Sci. USA* (1985) 82: 7212; Talmadge et al., *Proc. Natl. Acad. Sci. USA* (1980) 77: 3988; Takahara et al., *J. Biol. Chem.* (1985) 260: 2670).

The fusion polypeptides of the invention can also be further linked to other bacterial proteins. This approach often results in high yields, because normal prokaryotic control sequences direct transcription and translation. In *E. coli*, lacZ fusions are often used to express heterologous proteins. Suitable vectors are readily available, such as the pUR, pEX, and pMR100 series (see, e.g., Sambrook et al., supra.). For certain applications, it may be desirable to cleave the non-glycosyltransferase and/or accessory enzyme amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one fusion polypeptide may be expressed in a single host cell by placing multiple transcriptional cassettes in a single expression vector, or by utilizing different selectable markers for each of the expression vectors which are employed in the cloning strategy.

A suitable system for obtaining recombinant proteins from *E. coli* which maintains the integrity of their N-termini has been described by Miller et al. *Biotechnology* 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, plant cells, or microorganisms, such as, for example, yeast cells, bacterial cells, or fungal cells. Examples of suitable host cells include, for example, *Azotobacter* sp. (e.g., *A. vinelandii*), *Pseudomonas* sp., *Rhizobium* sp., *Erwinia* sp., *Escherichia* sp. (e.g., *E. coli*), *Bacillus*, *Pseudomonas*, *Proteus*, *Salmonella*, *Serratia*, *Shigella*, *Rhizobia*, *Vitreoscilla*, *Paracoccus* and *Klebsiella* sp., among many others. The cells can be of any of several genera, including *Saccharomyces* (e.g., *S. cerevisiae*), *Candida* (e.g., *C. utilis*, *C. parapsilosis*, *C. krusei*, *C. versatilis*, *C. lipolytica*, *C. zeylanoides*, *C. guilliermondii*, *C. albicans*, and *C. humicola*), *Pichia* (e.g., *P. farinosa* and *P. ohmeri*), *Torulopsis* (e.g., *T. candida*, *T. sphaerica*, *T. xylinus*, *T. famata*, and *T. versatilis*), *Debaryomyces* (e.g. *D. subglobosus*, *D. cantarellii*, *D. globosus*, *D. hansenii*, and *D. japonicus*), *Zygosaccharomyces* (e.g., *Z. rouxii* and *Z. bailii*), *Kluyveromyces* (e.g., *K. marxianus*), *Hansenula* (e.g., *H. anomala* and *H. jadinii*), and *Brettanomyces* (e.g., *B. lambicus* and *B. anomalus*). Examples of useful bacteria include, but are not limited to, *Escherichia*, *Enterobacter*, *Azotobacter*, *Erwinia*, *Klebsielia*,.

The expression vectors of the invention can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

In preferred embodiments, fusion polypeptides that comprise eukaryotic glycosyltransferase and accessory enzyme catalytic domains are expressed in eukaryotic host cells. Similarly, fusion polypeptides that comprise prokaryotic catalytic domains are preferably expressed in prokaryotic cells. Alternatively, one can express a mammalian fusion polypeptide in a prokaryotic host cell (see, e.g., Fang et al. (1998) *J. Am. Chem. Soc.* 120: 6635–6638), or vice versa.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred. Once purified, partially or to homogeneity as desired, the polypeptides may then be used (e.g., as immunogens for antibody production).

To facilitate purification of the fusion polypeptides of the invention, the nucleic acids that encode the fusion polypeptides can also include a coding sequence for an epitope or "tag" for which an affinity binding reagent is available. Examples of suitable epitopes include the myc and V-5 reporter genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the glycosyltransferase and accessory enzyme catalytic domains without diminishing their biological activity. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction sites or termination codons or purification sequences.

E. Uses of the Fusion Polypeptides

The invention provides methods of using fusion polypeptides produced using the methods described herein to prepare desired oligosaccharides (which are composed of two or more saccharides). The glycosyltransferase reactions of the invention take place in a reaction medium comprising at least one glycosyltransferase, an acceptor sugar and typically a soluble divalent metal cation. Substrates for the accessory enzyme catalytic moiety are also present, so that the accessory enzyme can synthesize the donor moiety for the glycosyltransferase. The methods rely on the use of a glycosyltransferase to catalyze the addition of a saccharide to a substrate saccharide. For example, the invention provides methods for adding sialic acid to a galactose residue in an α2,3 linkage, by contacting a reaction mixture that includes an acceptor moiety comprising a Gal residue in the presence of an α2,3-sialyltransferase/CMP-NeuAc synthetase fusion polypeptide that has been prepared according to the methods described herein. The reaction mixture also includes sialic acid and CTP, as well as other ingredients necessary for activity of the sialyltransferase and the CMP-NeuAc synthetase.

A number of methods of using glycosyltransferases to synthesize desired oligosaccharide structures are known. Exemplary methods are described, for instance, WO 96/32491, Ito et al. (1993) *Pure Appl. Chem.* 65: 753, and U.S. Pat. Nos. 5,352,670, 5,374,541, and 5,545,553.

The fusion polypeptides prepared as described herein can be used in combination with additional glycosyltransferases. For example, one can use a combination of sialyltransferase fusion polypeptide and a galactosyltransferase, which may or may not be part of a fusion polypeptide. In this group of embodiments, the enzymes and substrates can be combined in an initial reaction mixture, or preferably the enzymes and reagents for a second glycosyltransferase reaction can be added to the reaction medium once the first glycosyltransferase reaction has neared completion. By conducting two glycosyltransferase reactions in sequence in a single vessel, overall yields are improved over procedures in which an intermediate species is isolated. Moreover, cleanup and disposal of extra solvents and by-products is reduced.

The products produced by the above processes can be used without purification. However, it is usually preferred to recover the product. Standard, well known techniques for recovery of glycosylated saccharides such as thin or thick layer chromatography, ion exchange chromatography, or membrane filtration can be used. It is preferred to use membrane filtration, more preferably utilizing a nanofiltration or reverse osmotic membrane as described in commonly assigned U.S. patent application Ser. No. 08/947,775, filed Oct. 9, 1997. For instance, membrane filtration wherein the membranes have molecular weight cutoff of about 1000 to about 10,000 can be used to remove proteins. Nanofiltration or reverse osmosis can then be used to remove salts. Nanofilter membranes are a class of reverse osmosis membranes which pass monovalent salts but retain polyvalent salts and uncharged solutes larger than about 200 to about 1000 Daltons, depending upon the membrane used. Thus, in a typical application, the oligosaccharides of the invention will be retained in the membrane and contaminating salts will pass through.

EXAMPLES

The following examples are offered to illustrate, but not to limit the present invention.

Example 1

Construction of a CMP-Neu5Ac Synthetase/α2,3-Sialyltransferase Fusion Protein

This Example describes the construction and expression of a polynucleotide that encodes a fusion protein that has both CMP-Neu5Ac synthetase activity and α2,3-sialyltransferase activity. Large-scale enzymatic synthesis of oligosaccharides containing terminal N-acetyl-neuraminic acid residues requires large amounts of the sialyltransferase and the corresponding sugar-nucleotide synthetase for the synthesis of the sugar-nucleotide donor, CMP-Neu5Ac, an unstable compound. Using genes cloned from *Neisseria meningitidis*, we constructed a fusion protein which has both CMP-Neu5Ac synthetase and α-2,3-sialyltransferase activities. The fusion protein was produced in high yields (over 1,200 units per liter, measured using an α-2,3-sialyltransferase assay) in *Escherichia coli* and functionally pure enzyme could be obtained using a simple protocol. In small-scale enzymatic syntheses, we showed that the fusion protein could sialylate various oligosaccharide acceptors (branched and linear) with N-acetyl-neuraminic acid as well as N-glycolyl- and N-propionyl-neuraminic acid in high conversion yield. The fusion protein was also used to produce α-2,3-sialyllactose at the 100 g scale using a sugar nucleotide cycle reaction, starting from lactose, sialic acid, phosphoenolpyruvate and catalytic amounts of ATP and CMP.

Previously we reported the cloning and over-expression in *Escherichia coli* of both the CMP-Neu5Ac synthetase (Gilbert et al. (1997) *Biotechnol. Lett.* 19: 417–420) and the α-2,3-sialyltransferase (Gilbert et al. (1996) *J. Biol. Chem.* 271: 28271–28276; Gilbert et al. (1997) *Eur. J. Biochem.* 249: 187–194) from *Neisseria meningitidis*. The two enzymes were used together to synthesize milligram amounts of sialyllactose, sialyl-N-acetyllactosamine and sialyl-P$^k$ (Neu5Ac-α-(2→3)-Gal-α-(1→4)-Gal-β-(1→4)-Glc). The CMP-Neu5Ac synthetase can also be used to produce CMP derivatives of sialic acid analogs in order to synthesize the corresponding sialo-oligosaccharide analogs (Id.).

Although we obtained a high yield (750 U/L) of the α-2,3-sialyltransferase in *E. coli* (Id.), the purified enzyme was relatively insoluble and had a tendency to precipitate and lose activity during storage. Since the CMP-Neu5Ac synthetase was necessary for synthesis purposes and was a soluble enzyme, we decided to make a fused form of these two enzymes to see if it would be more soluble than the individual α-2,3-sialyltransferase. The following two reactions would therefore be catalyzed by the same polypeptide:

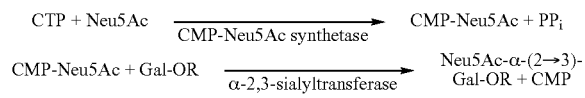

The fused form of these enzymes would also be kinetically favorable since the CMP-Neu5Ac synthetase has a turnover number (Gilbert et al. (1997) *Biotechnol. Lett.* 19: 417–420) of 31.4 sec$^{-1}$ while the α-2,3-sialyltransferase has turnover numbers ranging from 0.1 to 1.4 sec$^{-1}$, depending on the acceptor (Gilbert et al. (1997) *Eur. J. Biochem.* 249: 187–194 and unpublished data). The fused form would have the additional benefit of reducing enzyme production costs by having a single culture to grow and a single product to purify to obtain the two activities.

Materials and Methods

Construction of the Fusion CMP-Neu5Ac Synthetase/α-2,3-sialyltransferase.

PCR was performed with Pwo polymerase as described by the manufacturer (Boehringer Mannheim, Laval, Que.). The *Neisseria* CMP-Neu5Ac synthetase was amplified using SYNTM-F1 as the 5' primer (41 mer: 5'-CTTAGGAGGT-CATATGGAAAAACAAAATATTGCGGTTATAC-3' (SEQ ID NO: 3); the NdeI site is in italics) and SYNTM-R6 as the 3' primer (45-mer: 5'-CGACAGAATTCCGCCAC-CGCTTTCCTTGTGATTAAGAATGTTTTC-3' (SEQ ID NO: 4); the EcoRI site is in italics) and pNSY-01 (Gilbert et al. (1997) *Biotechnol. Lett.* 19: 417–420) as the template.

The *Neisseria* α-2,3-sialyltransferase was amplified using SIALM-22F as the 5' primer (37-mer: 5'-GCATGGAAT-TCTGGGCTTGAAAAAGGCTTGTTTGACC-3' (SEQ ID NO: 5); the EcoRI site is in italics) and SIALM-23R as the 3' primer (59-mer: 5'-CCTAGGTCGACTCATTAGTGGT-GATGGTG GTGATGGTTCAGGTCTTCTTCG-CTGAT-CAG-3' (SEQ ID NO: 6); the SalI site is in italics, the 6-His (SEQ ID NO:14) tail is underlined and the c-myc tag is in bold) and using pNST-09 (Gilbert et al. (1996) *J. Biol. Chem.* 271: 28271–28276) as the template. The plasmid pFUS-01 was constructed by digesting the CMP-Neu5Ac synthetase PCR product with NdeI and EcoRI and the α-2,3-sialyltransferase PCR product with EcoRI and SalI and cloning them in a modified version of pCWori+ (Gilbert et al. (1997) *Eur. J. Biochem.* 249: 187–194), in which the lacZα gene fragment has been deleted.

Expression in *E. coli* and Purification of the Fusion Protein

The initial screening of pFUS-01 versions was done using *E. coli* BMH71-18 as the host. For the large-scale production of the fusion protein we used *E. coli* AD202 (CGSC #7297). A 21 L culture of *E. coli* AD202/pFUS-01/2 was grown in a 28-L New Brunswick Scientific (Edison, N.J.) fermenter (model MF 128S) as described previously (Gilbert et al. (1997) *Eur. J. Biochem.* 249: 187–194). The cells were resuspended in 50 mM Hepes pH 7 at a ratio of 20 g of wet cell paste for 80 mL of buffer. Cell extracts were prepared using an Avestin C5 Emulsiflex cell disrupter (Avestin, Ottawa, Ont.). Polyethylene glycol (average molecular weight 8,000 Da) and NaCl were added to 4% and 0.2 M, respectively, and the cell extract was stirred 20 min at 4° C. The extract was centrifuged 20 min at 8000 rpm and the pellet was washed twice with 50 mM Hepes pH 7, 0.2 M NaCl, 4% PEG. The pellet was resuspended with 50 mM Tris, pH 7.5, 1 mM EDTA and Triton X-100 (reduced and peroxide-free) was added to 1% v/v. The resuspended pellet was stirred 30 min at 4° C. and then clarified by centrifugation for 1 h at 13,000×g. The supernatant was applied to two 5-mL HiTrap Chelating column (Pharmacia Biotech, Uppsala, Sweden) charged with Ni$^{2+}$, the maximum load being 25 mg total protein in each run. The columns were developed with a 60–800 mM imidazole gradient in 10 mM Hepes (pH 7) containing 0.5 M NaCl and 0.2% Triton X-100.

Assays

Protein concentration was determined using the bicinchoninic acid protein assay kit from Pierce (Rockford, Ill.). For all of the enzymatic assays one unit of activity was defined as the amount of enzyme that generated one μmol of product per minute. The CMP-Neu5Ac synthetase activity was assayed at 37° C. using 3 mM Neu5Ac, 3 mM CTP, 100 mM Tris pH 8.5, 0.2 mM DTT and 10 mM MgCl$_2$ in a final volume of 50 μL. The reaction was stopped after 10 min by adding EDTA to 20 mM final concentration and the reaction mixture was analyzed by capillary electrophoresis performed with a Beckman Instruments (Fullerton, Calif.) P/ACE 5510 equipped with a P/ACE diode array detector set at 271 nm and using the separation conditions described previously (Gilbert et al. (1997) *Biotechnol. Lett.* 19: 417–420).

All acceptors were synthesized as previously described (Gilbert et al. (1997) *Eur. J. Biochem.* 249: 187–194; Wakarchuk et al. (1996) *J. Biol. Chem.* 271: 19166–19173) with the exception that FEX (# F-6130, Molecular Probes, Eugene, Oreg.) was used in place of FCHASE for the LacNAc acceptor.

The α-2,3-sialyltransferase activity was assayed at 37° C. using 0.5 mM LacNAc-FEX, 0.2 mM CMP-Neu5Ac, 50 mM Mes pH 6.0, 10 mM MnCl$_2$ in a final volume of 10 μL. After 5 min the reactions were terminated by dilution with 10 mM NaOH and analyzed by capillary electrophoresis performed using the separation conditions described previously (Gilbert et al. (1997) *Eur. J. Biochem.* 249: 187–194).

The coupled assay was performed using similar conditions except that the incubation time was 10 min and the reaction mixture included 0.5 mM LacNAc-FEX, 3 mM CTP, 3 mM Neu5Ac, 100 mM Tris pH 7.5, 0.2 mM DTT and 10 mM MgCl$_2$. The same reagent concentrations were used when the alternate acceptors (Lac-FCHASE and P$^k$-FCHASE) or the alternate donors (Neu5Gc and Neu5Pr) were tested, except the reaction times were 60 to 120 mm.

Sialylation of a biantennary acceptor was performed using 1 mg of Gal-β-(1→4)-GlcNAc-β-(1→2)-Man-α-(1→6)-[Gal-β-(1→4)-GlcNAc-β-(1→2)-Man-α-(1→3)-]-MAN-β-(1→4)-GlcNAc-β-(1→4)-GlcNAc in a 90 min reaction. Reaction progress was monitored by TLC using isopropanol/H$_2$O /ammonium hydroxide (6:3:1) to develop the plate and the sialylated product was purified by gel filtration on Bio-Gel P-4 (Bio-Rad Lab., Hercules, Calif.). The mass of the isolated compound was determined by mass spectrometry (negative ion mode).

Use in a 100 g Scale Synthesis

The reaction was performed in a total volume of 2.2 L and the following reagents were added sequentially: lactose monohydrate (59.4 g, 0.165 mol), phospho-enolpyruvate monopotassium salt (34 g, 0.165 mol), bovine serum albumin (2.2 g), sialic acid (51 g, 0.165 mol), CMP (2.84 g, 8.79 mmol), ATP (0.532 g, 0.879 mmol) and sodium azide (0.44 g). The pH was adjusted to 7.4 with NaOH and MnCl$_2$ was added to a final concentration of 30 mM. The reaction was allowed to proceed at room temperature after the addition of 13,200 units of myokinase (Boehringer Mannheim), 19,800 units of pyruvate kinase (Boehringer Mannheim) and 820 units (based on α-2,3-sialyltransferase activity) of fusion protein obtained by extraction with Triton X-100 of the PEG/NaCl precipitate. Reaction progress was monitored daily by TLC using isopropanol/H$_2$O /ammonium hydroxide (7:2:1) to develop the plate and orcinol/sulfuric acid followed by heating to visualize the product. Mn$^{2+}$ was monitored daily by ion chromatography and the reaction mixture was supplemented with 1M MnCl$_2$ to maintain a final concentration of 30 mM. Supplementary phosphoenolpyruvate was added after two days (0.165 mol) and four days (0.055 mol).

After a total reaction time of 6 days, the crude α-2,3-sialyllactose solution was filtered through two sheets of Whatman filter paper to remove the precipitate producing a yellow filtrate. Proteins were then removed by tangential flow ultrafiltration using a 3,000 MWCO membrane (#P2PLBCC01, Millipore, Bedford, Mass.), providing a clear yellow solution. Triton X-100 was removed from the reaction mixture by filtration through a column containing 500 g of C18 reverse phase resin. The eluate was then further purified using a nanofiltration machine (#19T-SSXYC-PES-316-SP, Osmonics, Minnetonka, Minn.) fitted with a spiral wound membrane (#GE2540C1076) and using two different pH's. The pH of the solution was first adjusted with concentrated HCl to pH=3.0, and the feed solution was recirculated for 10 hours while maintaining the total volume of the feed by continuous addition of deionized water. When the conductivity of the permeate solution reached 22 mS, the pH was adjusted to pH=7.0 with 50% NaOH. Recirculation of this solution while maintaining the feed volume with deionized water was performed for an additional 2 hours. The feed solution was concentrated to 800 mL and was then treated with AG50WX8 (H+) Dowex resin until a pH of 2.0 was reached. After removing the resin by filtration, the pH was adjusted to 7.0 with NaOH and the solution was decolorized by passing through activated charcoal. The solution was finally lyophilized to yield a white powder and the α-2,3-sialyllactose content was determined by $^1$H NMR analysis in D$_2$O using 1,2-isopropylidene-α-D-glucofuranose as the reference standard.

Results

Construction of the Fusion CMP-Neu5Ac Synthetase/α-2,3-sialyltransferase

The *Neisseria* CMP-Neu5Ac synthetase was amplified by PCR, using primers that included a NdeI site (5') and an EcoRI site (3'), while the *Neisseria* α-2,3-sialyltransferase was amplified using primers that included an EcoRI site (5') and a SalI site (3'). The two PCR products were cloned together in a modified version of pCWori+ (Gilbert et al. (1997) *Eur. J. Biochem.* 249: 187–194) that was digested with NdeI and SalI. In the resulting construct (pFUS-01) the start codon of the CMP-Neu5Ac synthetase was downstream of the three sequential IPTG-inducible promoters and the ribosome binding site present in pCWori+. The α-2,3-sialyltransferase was linked to the C-terminal of the CMP-Neu5Ac synthetase through a 4-residue peptide linker (Gly-Gly-Gly-Ile; SEQ ID NO:18) and the C-terminus of the fusion protein includes a c-Myc epitope tag for immunodetection and a His$_6$ (SEQ ID NO:14) tail for purification by immobilized metal affinity chromatography (IMAC). In the process of cloning pFUS-01 we also obtained 2 clones that included additional residues in the linker regions. The linker of pFUS-01/2 (see FIG. 1) is 9 residues long (Gly-Gly-Gly-Ile-Leu-Ser-His-Gly-Ile; SEQ ID NO: 7) while the linker of pFUS-01/4 is 8 residues long (Gly-Gly-Gly-Ile-Leu-Ser-Gly-Ile; SEQ ID NO: 8). Analysis by DNA sequencing of the two versions with additional residues suggested that they were cloning artifacts due to incomplete restriction enzyme digestion of the PCR products.

Expression in *E. coli* and Purification of the Fusion Protein

*E. coli* BMH71-18 was transformed with the three versions of pFUS-01 and the level of α-2,3-sialyltransferase activity was compared in small-scale cultures (20 mL). The highest activity was obtained with pFUS-01/2, which gave 40% more activity than pFUS-01/4 and 60% more activity than pFUS-01. The fusion protein encoded by pFUS-01/2 has the longest linker which might aid the independent folding of the two components. However, the effects of linker composition and length were not further studied and pFUS-01/2 was used for the scale-up in production and kinetics comparison.

Since we had observed an OmpT-catalyzed degradation when pFUS-01/2 was expressed in *E. coli* BMH71-18 (data not shown) we used an ompT-deficient host strain (*E. coli* AD202) for expression. In a 21 L culture of *E. coli* AD202/pFUS-01/2, we measured a production of 1,200 U per liter using an assay for α-2,3-sialyltransferase activity, 11,500 U per liter using an assay for CMP-Neu5Ac synthetase activity and 300 U per liter using a coupled CMP-Neu5Ac synthetase/α-2,3-sialyltransferase assay. SDS-PAGE analysis indicated that a band with the expected molecular mass (70.2 kDa) of the fusion enzyme was predominant in the extract. The activity was associated with the insoluble fraction of the extract since over 95% of the activity was recovered in the pellet when the extract was centrifuged at 100,000×g for 1 hour. This situation was similar to what we observed with the separate α-2,3-sialyltransferase when it was over-expressed in E. coli (Id.). The α-2,3-sialyltransferase is membrane bound in N. meningitidis (Gilbert et al. (1996) J. Biol. Chem. 271: 28271–28276) and it is not surprising that, when over-expressed separately or as a fusion protein in E. coli, part of it was associated with the membranes and/or cell debris.

In order to avoid large-scale ultracentrifugation, we developed a precipitation strategy to recover the activity associated with the insoluble fraction at a lower centrifugation speed (12,000×g). Precipitation with 4% polyethylene glycol (PEG 8000) and 0.2 M NaCl afforded over 95% recovery of activity in the pellet, with a 1.8 fold increase in specific activity between the crude extract (0.32 U/mg) and the PEG/NaCl precipitate (0.58 U/mg). The pellet was washed with buffer containing PEG/NaCl in order to remove traces of soluble (cytosolic) enzymes such as hydrolases that could degrade essential co-factors and substrates used in the enzymatic synthesis of target oligosaccharides. Although the washing steps reduced slightly the enzyme recovery, it was essential to obtain functionally pure fusion protein.

The PEG/NaCl precipitate was extracted with 1% Triton X-100 in order to solubilize the activity. We recovered 60–70% of the enzyme activity in the soluble fraction which represented a 40–55% yield when compared with the activity present in the total extract and a 3 fold increase in specific activity (1 U/mg). The material extracted with Triton X-100 from the PEG/NaCl precipitate was stable for at least a month at 4° C. and was used in the synthesis reactions described below.

Immobilized metal affinity chromatography (IMAC) was performed on the Triton X-100 extract and the fusion protein appeared in the fractions eluting between 400 and 550 mM imidazole. The purified fusion protein had a specific activity of 1–2 U/mg and the overall purification yield was below 5%. Analysis of the purified protein by SDS-PAGE showed that it was at least 90% pure.

Comparison of the Fusion Protein with the Individual Enzymes

This comparison was made difficult by the fact that the enzymes differ widely in their solubility and tendency to aggregate when purified to homogeneity. We observed previously that the CMP-Neu5Ac synthetase was soluble to above 20 mg/mL (Gilbert et al. (1997) Biotechnol. Lett. 19: 417–420) while the α-2,3-sialyltransferase precipitated when attempts were made to concentrate it above 1 mg/mL, even in the presence of detergent (Gilbert et al. (1997) Eur. J. Biochem. 249: 187–194). The IMAC-purified fusion protein was soluble to about 5 mg/mL in the presence of 0.2% Triton X-100. Using the α-2,3-sialyltransferase assay we found specific activities in the range of 1 to 1.5 U/mg for different batches of the purified separate α-2,3-sialyltransferase and 1 to 2 U/mg for different batches of the purified fusion protein. A tendency to aggregate might explain the relatively large variation in specific activity between different batches of IMAC-purified fusion protein.

Previously we observed that partially purified α-2,3-sialyltransferase could be extracted with Triton X-100 from membrane fractions obtained by ultracentrifugation (Id.). This procedure is similar to the extraction of the fusion protein from the PEG/NaCl precipitate but the extraction from the membranes yielded purer material. Such preparations of both the fusion protein and the separate α-2,3-sialyltransferase were more stable than the IMAC-purified material, but since the enzyme was not homogeneous the protein concentration was estimated by scanning densitometry of SDS-PAGE gels. Using this procedure we observed a specific activity of 2.0 U/mg for the separate α-2,3-sialytransferase and 2.7 U/mg for the fusion protein. When taking into account the molecular masses of these two proteins, we calculated turnover numbers of 1.4 $sec^{-1}$ for the separate α-2,3-sialyltransferase and 3.2 $sec^{-1}$ for the fusion enzyme. Given the different solubility properties of these two proteins, it is difficult to conclude if there is any real catalytic improvement of the α-2,3-sialyltransferase when it is in the fused form or if it is simply more stable under the assay conditions. On the other hand, the CMP-Neu5Ac synthetase turnover number of the fused form was comparable to the turnover number of the separate CMP-Neu5Ac synthetase (39.5 $sec^{-1}$ and 31.4 $sec^{-1}$, respectively).

Small Scale Syntheses with Various Donors and Acceptors

The ability of the fusion protein to use different donors and acceptors was tested in analytical (5 nmol) coupled reactions performed at pH 7.5 which is intermediate between the optimal pH of the α-2,3-sialyltransferase (pH 6) (Gilbert et al. (1996) J. Biol. Chem. 271: 28271–28276) and the optimal pH of the CMP-Neu5Ac synthetase (pH 8.5) (Warren and Blacklow (1962) J. Biol. Chem. 237: 3527–3534). The fusion protein could sialylate N-acetyllactosamine-FEX and lactose-FCHASE with N-acetyl-neuraminic acid as well as the N-propionyl- and N-glycolyl- analogs in yields that exceeded 97% in 1 hour (Table 1). Both N-acetyl-lactosamine-FEX and lactose-FCHASE have a terminal β-Gal which is the natural acceptor for the Neisseria α-2,3-sialyltransferase (Gilbert et al. (1997) Eur. J. Biochem. 249: 187–194).

TABLE 1

Small-scale syntheses using the fusion CMP-Neu5Ac synthetase/α-2,3-sialyltransferase with various donors and acceptors (% conversion to sialylated product).

| Acceptor | Donor[a] | | |
| --- | --- | --- | --- |
| | Neu5Ac | Neu5Pr | Neu5Gc |
| Gal-β-(1→4)-GlcNAc-β[b] (60 min reaction) | >99 | >99 | >99 |
| Gal-β-(1→4)-Glc-β[c] (60 min reaction) | >99 | 97 | 97 |

TABLE 1-continued

Small-scale syntheses using the fusion CMP-Neu5Ac synthetase/α-2,3-sialyltransferase with various donors and acceptors (% conversion to sialylated product).

| Acceptor | Donor[a] | | |
|---|---|---|---|
| | Neu5Ac | Neu5Pr | Neu5Gc |
| Gal-α-(1→4)-Gal-β-(1→4)-β-Glc-β[c] (120 min reaction) | 84 | 84 | 55 |
| Biantennary N-linked type[d] (90 min reaction) | >99 | ND[e] | ND |

[a]Neu5Ac = N-acetyl-neuraminic acid
Neu5Pr = N-propionyl-neuraminic acid
Neu5Gc = N-glycolyl-neuraminic acid
[b]This acceptor was a FEX-aminophenyl-glycoside derivative.
[c]These acceptors were FCHASE-aminophenyl-glycosides derivatives.

[d]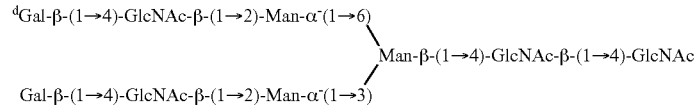

[e]Not determined.

When P[k]-FCHASE (Gal-α-(1→4)-Gal-β-(1→4)-Glc-FCHASE) was used as the acceptor in 2 hour reactions, the sialylation yield was 84% with either N-acetyl- or N-propionyl-neuraminic acid while it was 55% with N-glycolyl-neuraminic acid (Table 1). We had observed previously that P[k]-FCHASE was a substrate for the α-2,3-sialyltransferase but it was found to have a $k_{cat}/K_m$ 4 to 40-fold lower than substrates which have terminal β-Gal (Gilbert et al. (1997) *Eur. J. Biochem.* 249: 187–194). N-glycolyl-neuraminic acid gave the lowest sialylation yields with the three acceptors tested, which is not surprising since the *Neisseria* CMP-Neu5Ac synthetase had a $K_m$ that was 8-fold higher with N-glycolyl-neuraminic acid than with N-acetyl-neuraminic acid (Gilbert et al. (1997) *Biotechnol. Lett.* 19: 417–420).

The fusion protein can also use branched oligosaccharides as acceptors since we observed >99% sialylation of an asialo- galactosylated biantennary N-linked type oligosaccharide using N-acetyl-neuraminic acid as the donor (Table 1). This reaction was done at the 1 mg scale using the underivatized oligosaccharide and the mass of the isolated product (2224.0 Da) was found to agree with the mass of the expected di-sialylated biantennary oligosaccharide (2223.3 Da).

Use in a 100 g Scale Synthesis

The material extracted with Triton X-100 from the PEG/NaCl precipitate was used in a 100 g scale synthesis to produce α-2,3-sialyllactose using the sialyltransferase cycle (Ichikawa et al. (1991) *J. Am. Chem. Soc.* 113: 4698–4700) starting from lactose, sialic acid, phosphoenolpyruvate (PEP), and catalytic amounts of ATP and CMP. After 6 days of reaction, the reaction had reached completion as evidenced by the disappearance of sialic acid by TLC analysis. The product was then purified by a sequence of ultrafiltration, nanofiltration and ion exchange. This process yielded 77 g of a white solid which had an α-2,3-sialyllactose content of 88% and a water content of 7%. Based on the α-2,3-sialyllactose content of the isolated product, the overall yield for the synthesis and isolation was 68%.

Discussion

The CMP-Neu5Ac synthetase/α-2,3-sialyltransferase fusion protein was expressed at high level in a cost-effective expression system and showed both enzyme activities at levels comparable to those of the individual enzymes. It was readily recoverable by a simple protocol involving precipitation and detergent extraction, therefore avoiding expensive chromatographic steps. The detergent extracted fusion protein was functionally pure, i.e. it was free from contaminating enzyme activities that can hydrolyze sugar nucleotides or other components of the cofactor regeneration system.

To be useful for large scale carbohydrate synthesis the fusion protein should be applicable in a sugar nucleotide cycle. This cycle is designed to use only catalytic amounts of expensive sugar nucleotides and nucleoside phosphates, which are enzymatically regenerated in situ from low-cost precursors. The recycling of the converted co-factors also prevents end-product inhibition. The α-2,3-sialyllactose 100 g scale synthesis went to completion, which is important since stoichiometric conversion of substrates is desirable not only to minimize reagent costs but also because it greatly simplifies the purification of the product from a large scale synthesis. Another interesting feature of the fusion protein is that it can use directly different donor analogs and various acceptors with a terminal galactose residue. Consequently it can be used for the synthesis of both natural carbohydrates and synthetic derivatives with novel properties.

The CMP-Neu5Ac synthetase/α-2,3-sialyltransferase fusion protein was expressed in high yield in *E. coli* with the two components being at least as active as the separate enzymes, which indicates that they were folded properly. This example suggests that construction and expression of fusion proteins may be of general utility to produce the enzymes required for large-scale biotechnological processes involving multiple enzymatic steps.

Example 2

Construction of a UDP-Glucose Epimerase /β-1,4-Galactosyltransferase Fusion Protein The use of sugar nucleotide cycling systems (SNC) oligosaccharide synthesis requires a number of enzymes. The purification of these enzymes is a time consuming and expensive part of the process. In the first example we produced a fusion protein which combines a transferase with its corresponding sugar-nucleotide synthetase (FUS-01), and have shown the advantages of a simple purification of the two activities. In this example we have produced a fusion of two other proteins used in SNC reactions, the UDP-Glucose 4 epimerase (galE) and a β-1,4-galactosyltransferase (lgtB).

Materials and Methods

DNA Manipulations

The *S. thermophilus* UDP-glucose 4' epimerase (galE) gene was amplified from pTGK-EP1 using primers derived from the nucleotide sequence of galE from *Streptococcus thermophilus* (GenBank accession M38175). GalE-5p was used as the 5' primer (58 mer: 5'-GGGACAGGATCCATC-GATGCTTAGGAGGTCATATGGCAATTT TAGTATTAG-GTGGAGC-3' (SEQ ID NO: 9); the BamHI site is in bold and italics)(primers used in this Example are shown in FIG. 4) and GalE-3p as the 3' primer (42-mer: 5'-GGGGGGGCTAGCGCCGCCTCCTCGATCATCG TACCCTTTTGG-3' (SEQ ID NO: 10); the NheI site is in italics). The plasmid pTGK/EP1, which includes the galE gene was used (see, PCT Patent Application Publ. No. WO98/20111) as the template.

The *Neisseria* β-1,4-galactosyltransferase was amplified using LgtB-NheI as the 5' primer (38-mer: 5'-GGGGGGGCTAGCGTGCAAAACCACGT-TATCAGCTTAGC-3' (SEQ ID NO: 11); the NheI site is in italics) and LgtB-SalI as the 3' primer (45-mer: 5'-GGGGGGGTCGACCTATTATTGGAAAG-GCACAATGAACTGTTCGCG-3' (SEQ ID NO: 12); the SalI site is in italics) and using pCW-1gtB(MC58) (Wakarchuk et al. (1998) *Protein Engineering* 11: 295–302) as the template. The thermocycler parameters were 94° C. 3 min., and 30 cycles of 55° C. 30 sec., 72° C. 30 sec., 94° C. 30 sec. PCR was performed with Pwo polymerase as described by the manufacturer (Boehringer Mannheim, Laval, Que.). The nucleotide (SEQ ID NO: 1) and deduced amino acid (SEQ ID NO: 2) sequences of the *Neisseria* β-1,4-galactosyltransferase are shown in FIG. 2.

Figure 3:
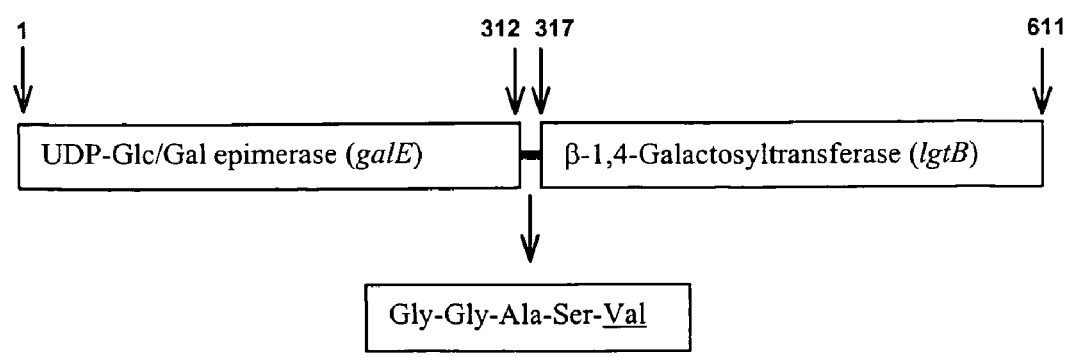
FIG. 3 shows a diagram of a recombinant fusion protein that catalyzes transfer of galactose residues from a donor to an acceptor. The C terminus of the UDP-Glc/Gal epimerase is linked covalently to the N terminus of the β-1,4-Galactosyltransferase through a 4-residue peptide linker. The first Met residue of the β-1,4-Galactosyltransferase was replaced by a Val residue (underlined in the linker sequence (SEQ ID NO:15)). The total length of the fusion protein encoded by pFUS-EB is 611 residues.

The plasmid pFUS-EB was constructed as follows (FIG. 3). The UDP-glucose 4 epimerase PCR product was digested with BamHI and NheI and the β-1,4-galactosyltransferase PCR product was digested with NheI and SalI and then recovered from the reaction mixtures using Prep-a-Gene™ resin according to the manufacturer's instruction (BioRad). The two genes were then combined in a three fragment ligation under standard conditions with the vector pCWori+ (Wakarchuk et al. (1994) *Protein Science* 3: 467–475) that had been digested with BamHI and SalI. DNA was introduced into *E. coli* DH12S using electroporation with 1 µl of the ligation reaction. Transformants were screened using colony PCR with primers specific for vector sequences flanking the cloning site. Colonies with inserts of the correct size, were then grown in liquid culture and tested for enzyme activity.

Determination of Enzyme Activity

Standard reactions for the β-1,4-galactosyltransferase enzyme were performed at 37° C. in 20 µl of: HEPES-NaOH buffer 50 mM, pH 7.5 containing, 10 mM $MnCl_2$, 1.0 mM fluorescein labeled acceptor, 1.0 mM UDP-Gal donor and various amounts of enzyme extract from recombinant *E. coli* that contains the cloned gene. The preparation of the fluorescein labeled acceptors was as described in Wakarchuk et al. (1996) *J. Biol. Chem.* 271 (32): 19166–19173 and Wakarchuk et al. (1998) *Protein Engineering* 11: 295–302.

Reactions to assess the epimerase-transferase fusion protein were performed with 1.0 mM UDP-Glucose in place of UDP-Gal. Enzymes were assayed after dilution of extracts in buffer containing 1 mg/ml acetylated bovine serum albumin. For calculation of enzyme activity, the enzyme dilutions were chosen such that for reaction times of 5–15 minutes approximately 10% conversion of the acceptor to product would be achieved. The reactions were terminated either by the addition of an equal volume of 2% SDS and heated to 75° C., for 3 minutes, or by diluting the reaction with 10 mM NaOH. These samples were then diluted appropriately in water prior to analysis by capillary electrophoresis (Wakarchuk et al. (1996) supra.).

Small scale extracts were made as follows. The cells were pelleted in an 1.5 ml microcentrifuge tube 2 min. at maximum speed, and the medium discarded. The pellet was frozen and then mixed with 2 volumes of 150 µm glass beads (Sigma), and ground with a glass pestle in the microcentrifuge tube. This mixture was then extracted twice with 50 µl of 50 mM HEPES-NaOH pH 7.5. The supernatant from this was used as the source of material for enzyme assays. Larger scale extractions and the PEG-8000 precipitation were performed as described in Gilbert et al. (1998) *Nature Biotechnology* 16: 769–772.

To verify that the product from reactions with the epimerase-transferase fusion using UDP-Glc was Gal-β-1,4-GlcNac-aminophenyl-FEX (FEX-LacNAc), reaction products were separated by TLC and then eluted in methanol. After drying under vacuum, the samples were dissolved in water and glycosidase assays were performed as described in Wakarchuk et al. (1996), supra. These samples were then analyzed by TLC against standards of the FEX-LacNAc and the degradation product, FEX-GlcNAc (data not shown).

Results

The pFUS-EB construct was investigated for its induction kinetics. The fusion protein was inducible, but the enzyme activity accumulates to its highest level in shake flasks without any IPTG being added. Activity of the fusion protein was measured with either UDP-Gal or UDP-Glc as the donor. Assays performed using FEX-GlcNAc as an acceptor show the amount of transferase activity using UDP-Glc as the donor is similar to the amount of transferase activity using UDP-Gal as the donor. The level of expression is such that from 1 L of shakeflask culture between 130–200 U of are produced.

With the CMP-NANA/α-2,3-sialyltransferase fusion protein, we have shown the utility of concentrating the enzyme with PEG-8000/NaCl precipitations (Example 1). We have investigated using PEG-8000/NaCl for recovery of the β-1, 4-galactosyltransferase fusion/UDP-glucose 4 epimerase fusion polypeptide from the cell free extracts. Since it appears to be a very soluble protein, we used 16% PEG-8000, which is a higher level than we had used for the other fusion protein. We did not see any adverse affects on enzyme activity after the PEG-8000 recovery step. It appears that the protein is not inhibited by the PEG precipitation step, and that recovery of active protein is high. It also appears that when the activity is measured in samples with higher concentrations of enzyme, using pre-formed UDP-Gal, that the activity is lower. This may be because the epimerase converts some of the UDP-Gal back to UDP-Glc, which makes the activity appear lower.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated nucleic acid that encodes a fusion polypeptide, wherein the fusion polypeptide comprises:
   a) a *Neisseria meningitidis* (*N. meningitidis*) α-2,3-sialyltransferase that catalyzes the transfer of a sialic acid, from CMP-Neu5Ac, to an acceptor molecule; and b) a *N. meningitidis* CMP-Neu5Ac synthetase that catalyzes the formation of CMP-Neu5Ac from Neu5Ac and CTP.

2. The nucleic acid of claim 1, wherein the *N. meningitidis* α-2,3-sialyltransferase and the *N. meningitidis* CMP-Neu5Ac synthetase are joined by a peptide linker.

3. The nucleic acid of claim 1, wherein the nucleic acid further comprises a polynucleotide that encodes a signal sequence which is linked to the fusion polypeptide.

4. The nucleic acid of claim 1, wherein the nucleic acid further comprises a polynucleotide that encodes a molecular tag which is linked to the fusion polypeptide.

5. An expression vector which comprises the nucleic acid of claim 1.

6. A host cell which comprises the expression vector of claim 5.

7. A method of producing a fusion polypeptide, the method comprising:
   a) introducing into a host cell the expression vector of claim 5, under conditions where the host cell is transformed with the expression vector; and
   b) culturing the said transformed host cell under conditions where the fusion polypeptide is expressed in the transformed host cell.

8. The method of claim 7 further comprising a step of purifying the expressed fusion polypeptide.

9. The method of claim 7 further comprising a step of permeabilizing the host cell expressing the fusion polypeptide.

10. The fusion polypeptide of claim 1, wherein the *N. meningitidis* CMP-Neu5Ac synthetase is encoded by a nucleic acid that is amplified by SEQ ID NO:3 and SEQ ID NO:4.

11. The fusion polypeptide of claim 1, wherein the *N. meningitidis* α-2,3-sialyltransferase is encoded by a nucleic acid that is amplified by SEQ ID NO:5 and SEQ ID NO:6.

12. The fusion polypeptide of claim 10, wherein the *N. meningitidis* α-2,3-sialyltransferase is encoded by a nucleic acid that is amplified by SEQ ID NO:5 and SEQ ID NO:6.

* * * * *

SEQUENCE LISTING

<160> NUMBER OF SEQ ID NOS: 18

<210> SEQ ID NO 1
<211> LENGTH: 828
<212> TYPE: DNA
<213> ORGANISM: Neisseria meningitidis
<220> FEATURE:
<221> NAME/KEY: CDS
<222> LOCATION: (1)..(828)
<223> OTHER INFORMATION: beta-1,4-galactosyltransferase (lgtB)

<400> SEQUENCE: 1

```
atg caa aac cac gtt atc agc tta gct tcc gcc gca gaa cgc agg gcg      48
Met Gln Asn His Val Ile Ser Leu Ala Ser Ala Ala Glu Arg Arg Ala
 1               5                  10                  15 cac att gcc gat acc ttc ggc agg cac ggc atc ccg ttt cag ttt ttc      96
His Ile Ala Asp Thr Phe Gly Arg His Gly Ile Pro Phe Gln Phe Phe
             20                  25                  30 gac gca ctg atg ccg tct gaa agg ctg gaa cag gca atg gcg gaa ctc     144
Asp Ala Leu Met Pro Ser Glu Arg Leu Glu Gln Ala Met Ala Glu Leu
         35                  40                  45 gtc ccc ggc ttg tcg gcg cac ccc tat ttg agc gga gtg gaa aaa gcc     192
Val Pro Gly Leu Ser Ala His Pro Tyr Leu Ser Gly Val Glu Lys Ala
     50                  55                  60 tgc ttt atg agc cac gcc gta ttg tgg aag cag gca ttg gac gaa ggt     240
Cys Phe Met Ser His Ala Val Leu Trp Lys Gln Ala Leu Asp Glu Gly
 65                  70                  75                  80 ctg ccg tat atc acc gta ttt gag gac gac gtt tta ctc ggc gaa ggt     288
Leu Pro Tyr Ile Thr Val Phe Glu Asp Asp Val Leu Leu Gly Glu Gly
                 85                  90                  95 gag gaa aaa ttc ctt gcc gaa gac gct tgg ctg caa gaa cgc ttt gac     336
Glu Glu Lys Phe Leu Ala Glu Asp Ala Trp Leu Gln Glu Arg Phe Asp
            100                 105                 110 ccg gat acc gcc ttt atc gtc cgc ttg gaa acg atg ttt atg cac gtc     384
Pro Asp Thr Ala Phe Ile Val Arg Leu Glu Thr Met Phe Met His Val
        115                 120                 125 ctg acc tcg ccc tcc ggc gtg gcg gat tac tgc ggg cgc gcc ttt ccg     432
Leu Thr Ser Pro Ser Gly Val Ala Asp Tyr Cys Gly Arg Ala Phe Pro
    130                 135                 140 ctg ttg gaa agc gaa cac tgg ggg acg gcg ggc tat atc att tcc cga     480
Leu Leu Glu Ser Glu His Trp Gly Thr Ala Gly Tyr Ile Ile Ser Arg
145                 150                 155                 160 aaa gcg atg cgg ttt ttc ctg gac agg ttt gcc gcc ctg ccg ccc gaa     528
Lys Ala Met Arg Phe Phe Leu Asp Arg Phe Ala Ala Leu Pro Pro Glu
                165                 170                 175 ggg ctg cac ccc gtc gat ctg atg atg ttc agc gat ttt ttc gac agg     576
Gly Leu His Pro Val Asp Leu Met Met Phe Ser Asp Phe Phe Asp Arg
            180                 185                 190 gaa gga atg ccg gtt tgc cag ctc aat ccc gcc ttg tgc gcc caa gag     624
Glu Gly Met Pro Val Cys Gln Leu Asn Pro Ala Leu Cys Ala Gln Glu
        195                 200                 205 ctg cat tat gcc aag ttt cac gac caa aac agc gca ttg ggc agc ctg     672
Leu His Tyr Ala Lys Phe His Asp Gln Asn Ser Ala Leu Gly Ser Leu
    210                 215                 220 atc gaa cac gac cgc ctc ctg aac cgc aaa cag caa agg cgc gat tcc     720
Ile Glu His Asp Arg Leu Leu Asn Arg Lys Gln Gln Arg Arg Asp Ser
225                 230                 235                 240 ccc gcc aac aca ttc aaa cac cgc ctg atc cgc gcc ttg acc aaa atc     768
Pro Ala Asn Thr Phe Lys His Arg Leu Ile Arg Ala Leu Thr Lys Ile
                245                 250                 255
```

```
agc agg gaa agg gaa aaa cgc cgg caa agg cgc gaa cag ttc att gtg    816
Ser Arg Glu Arg Glu Lys Arg Arg Gln Arg Arg Glu Gln Phe Ile Val
        260                 265                 270 cct ttc caa taa                                                    828
Pro Phe Gln
        275

<210> SEQ ID NO 2
<211> LENGTH: 275
<212> TYPE: PRT
<213> ORGANISM: Neisseria meningitidis

<400> SEQUENCE: 2

Met Gln Asn His Val Ile Ser Leu Ala Ser Ala Ala Glu Arg Arg Ala
 1               5                  10                  15

His Ile Ala Asp Thr Phe Gly Arg His Gly Ile Pro Phe Gln Phe Phe
            20                  25                  30

Asp Ala Leu Met Pro Ser Glu Arg Leu Glu Gln Ala Met Ala Glu Leu
        35                  40                  45

Val Pro Gly Leu Ser Ala His Pro Tyr Leu Ser Gly Val Glu Lys Ala
    50                  55                  60

Cys Phe Met Ser His Ala Val Leu Trp Lys Gln Ala Leu Asp Glu Gly
65                  70                  75                  80

Leu Pro Tyr Ile Thr Val Phe Glu Asp Asp Val Leu Leu Gly Glu Gly
                85                  90                  95

Glu Glu Lys Phe Leu Ala Glu Asp Ala Trp Leu Gln Glu Arg Phe Asp
            100                 105                 110

Pro Asp Thr Ala Phe Ile Val Arg Leu Glu Thr Met Phe Met His Val
        115                 120                 125

Leu Thr Ser Pro Ser Gly Val Ala Asp Tyr Cys Gly Arg Ala Phe Pro
    130                 135                 140

Leu Leu Glu Ser Glu His Trp Gly Thr Ala Gly Tyr Ile Ile Ser Arg
145                 150                 155                 160

Lys Ala Met Arg Phe Phe Leu Asp Arg Phe Ala Ala Leu Pro Pro Glu
                165                 170                 175

Gly Leu His Pro Val Asp Leu Met Met Phe Ser Asp Phe Phe Asp Arg
            180                 185                 190

Glu Gly Met Pro Val Cys Gln Leu Asn Pro Ala Leu Cys Ala Gln Glu
        195                 200                 205

Leu His Tyr Ala Lys Phe His Asp Gln Asn Ser Ala Leu Gly Ser Leu
    210                 215                 220

Ile Glu His Asp Arg Leu Leu Asn Arg Lys Gln Gln Arg Arg Asp Ser
225                 230                 235                 240

Pro Ala Asn Thr Phe Lys His Arg Leu Ile Arg Ala Leu Thr Lys Ile
                245                 250                 255

Ser Arg Glu Arg Glu Lys Arg Arg Gln Arg Arg Glu Gln Phe Ile Val
            260                 265                 270

Pro Phe Gln
        275

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence:SYNTM-F1 5'
      primer
```

-continued

```
<400> SEQUENCE: 3
cttaggaggt catatggaaa aacaaaatat tgcggttata c                    41

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence:SYNTM-R6 3'
      primer

<400> SEQUENCE: 4
cgacagaatt ccgccaccgc tttccttgtg attaagaatg ttttc                45

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:SIALM-22F 5'
      primer

<400> SEQUENCE: 5
gcatggaatt ctgggcttga aaaggcttg tttgacc                          37

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence:SIALM-23R 3'
      primer

<400> SEQUENCE: 6
cctaggtcga ctcattagtg gtgatggtgg tgatggttca ggtcttcttc gctgatcag  59

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence:linker of
      pFUS-01/2

<400> SEQUENCE: 7

Gly Gly Gly Ile Leu Ser His Gly Ile
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:linker of
      pFUS-01/4

<400> SEQUENCE: 8

Gly Gly Gly Ile Leu Ser Gly Ile
  1               5

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence:GalE-5p 5'
```

-continued primer

<400> SEQUENCE: 9
gggacaggat ccatcgatgc ttaggaggtc atatggcaat tttagtatta ggtggagc    58

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence:GalE-3p 3'
      primer

<400> SEQUENCE: 10 ggggggggcta gcgccgcctc ctcgatcatc gtacccttttt gg    42

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:LgtB-NheI 5'
      primer

<400> SEQUENCE: 11
gggggggcta gcgtgcaaaa ccacgttatc agcttagc    38

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence:LgtB-SalI 3'
      primer

<400> SEQUENCE: 12
gggggggtcg acctattatt ggaaaggcac aatgaactgt tcgcg    45

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence:peptide
      linker

<400> SEQUENCE: 13

Gly Gly Gly Ile Leu Ser His Gly Ile Leu
  1               5                  10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:6-His tail
      for purification

<400> SEQUENCE: 14

His His His His His His
  1               5

<210> SEQ ID NO 15
<211> LENGTH: 5
<212> TYPE: PRT
<213> ORGANISM: Artificial Sequence
<220> FEATURE:

```
<223> OTHER INFORMATION: Description of Artificial Sequence:peptide
      linker

<400> SEQUENCE: 15

Gly Gly Ala Ser Val
 1               5

<210> SEQ ID NO 16
<211> LENGTH: 63
<212> TYPE: DNA
<213> ORGANISM: Artificial Sequence
<220> FEATURE:
<223> OTHER INFORMATION: Description of Artificial Sequence:junction
      region of the galE-lgtB fusion
<221> NAME/KEY: CDS
<222> LOCATION: (1)..(63)
<223> OTHER INFORMATION: junction region of the galE-lgtB fusion

<400> SEQUENCE: 16 cca aaa ggg tac gat gat cga gga ggc gga gct agc gtg caa aac cac      48
Pro Lys Gly Tyr Asp Asp Arg Gly Gly Gly Ala Ser Val Gln Asn His
 1               5                  10                  15 gtt atc agc tta gct                                                  63
Val Ile Ser Leu Ala
            20

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence:junction
      region

<400> SEQUENCE: 17

Pro Lys Gly Tyr Asp Asp Arg Gly Gly Gly Ala Ser Val Gln Asn His
 1               5                  10                  15

Val Ile Ser Leu Ala
            20

<210> SEQ ID NO 18
<211> LENGTH: 4
<212> TYPE: PRT
<213> ORGANISM: Artificial Sequence
<220> FEATURE:
<223> OTHER INFORMATION: Description of Artificial Sequence:peptide
      linker

<400> SEQUENCE: 18

Gly Gly Gly Ile
 1
```